(12) United States Patent
Saito

(10) Patent No.: US 8,786,033 B2
(45) Date of Patent: Jul. 22, 2014

(54) BIOMETRIC SENSOR AND SENSOR PANEL, METHOD FOR DETECTING BIOMETRIC PATTERN USING THE SAME, AND METHOD FOR MANUFACTURING THE SAME

(75) Inventor: Tamio Saito, San Jose, CA (US)

(73) Assignee: IVI Holdings, Ltd., Boulder, CO (US)

(*) Notice: Subject to any disclaimer, the term of this patent is extended or adjusted under 35 U.S.C. 154(b) by 178 days.

(21) Appl. No.: 11/849,948

(22) Filed: Sep. 4, 2007

(65) Prior Publication Data

US 2008/0054875 A1 Mar. 6, 2008

Related U.S. Application Data

(60) Provisional application No. 60/842,055, filed on Sep. 1, 2006.

(51) Int. Cl.
*H01L 27/14* (2006.01)

(52) U.S. Cl.
USPC ........... 257/414; 257/350; 257/415; 257/124; 257/E51.001

(58) Field of Classification Search
USPC .................... 257/414, 350, 415, 124; 73/627; 382/124
See application file for complete search history.

(56) References Cited

U.S. PATENT DOCUMENTS

| 6,091,383 A * | 7/2000 | Borzea et al. ................... 345/76 |
| 6,716,642 B1 * | 4/2004 | Wu et al. ........................ 436/518 |
| 2004/0252867 A1 * | 12/2004 | Lan et al. ...................... 382/124 |

* cited by examiner

*Primary Examiner* — Davienne Monbleau
*Assistant Examiner* — Matthew Reames
(74) *Attorney, Agent, or Firm* — Marsh Fischmann & Breyfogle LLP; Daniel J. Sherwinter

(57) ABSTRACT

A biometric sensor panel includes (a) a first flexible substrate, (b) a plurality of first electrodes formed on the first flexible substrate, the first electrodes being arranged in a first direction, (c) a semiconductor layer formed on the first electrodes, (d) a second flexible substrate, (e) a plurality of second electrodes formed on the second flexible substrate, the second electrodes being arranged in a second direction crossing the first direction, and (f) a pressure sensitive conductive layer formed on the second electrodes, wherein the first and second flexible substrates face each other such that the semiconductor layer is in contact with the pressure sensitive conductive layer.

10 Claims, 36 Drawing Sheets

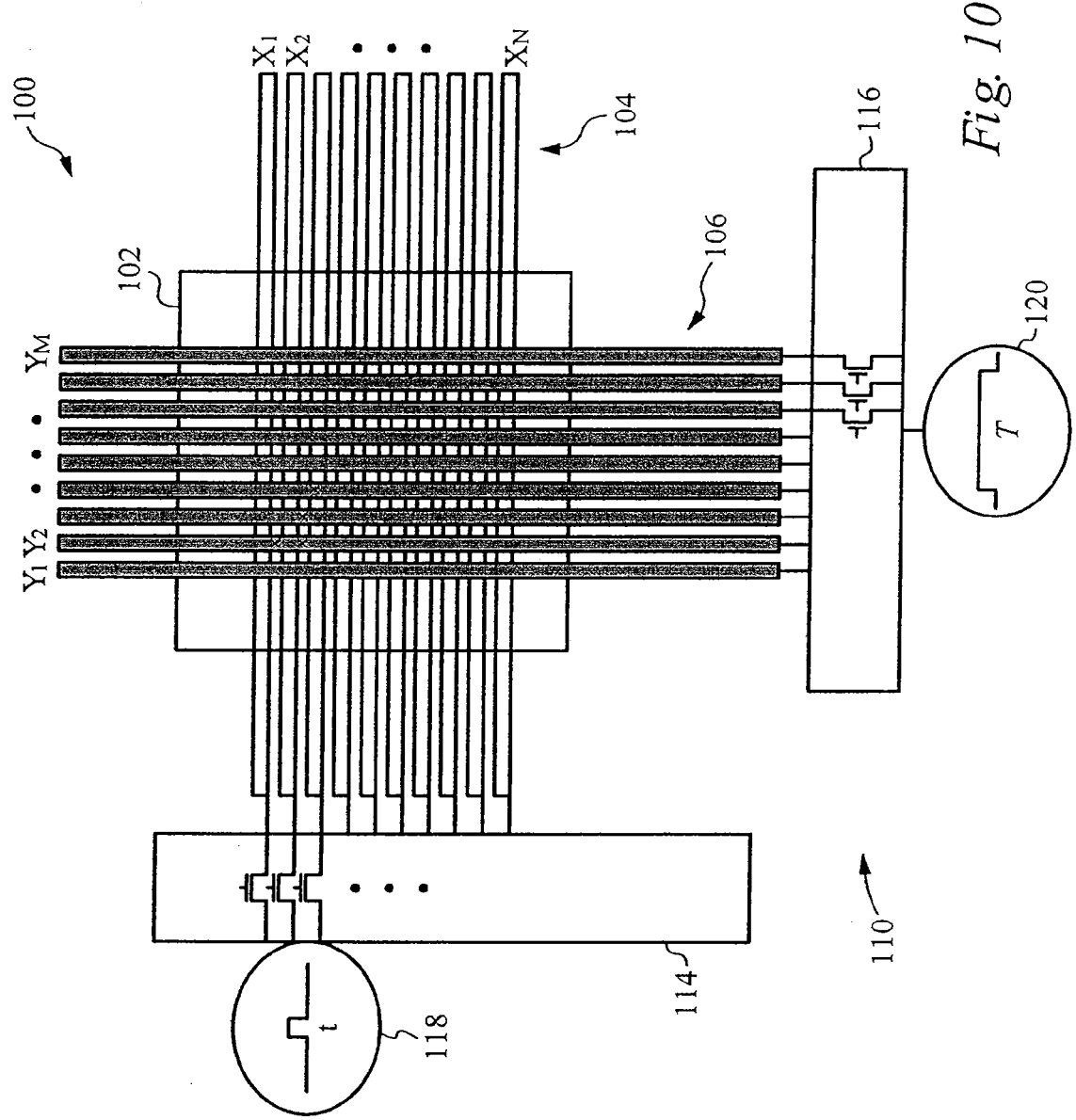

Developing

Ni Plating For Bumps

Au Plating For Bumps

BIOMETRIC SENSOR AND SENSOR PANEL, METHOD FOR DETECTING BIOMETRIC PATTERN USING THE SAME, AND METHOD FOR MANUFACTURING THE SAME

CROSS-REFERENCES TO RELATED APPLICATIONS

This application is related to U.S. Provisional Patent Application No. 60/731,385, entitled "Biometric Sensor, Method for Detecting Biometric Pattern Using The Same, and Method for Manufacturing The Same", filed on Oct. 28, 2005, and U.S. Provisional Patent Application No. 60/759,174, entitled "Biometric Sensor, Method for Detecting Biometric Pattern Using The Same, and Method for Manufacturing The Same", filed on Jan. 13, 2006, the entire disclosures of these applications are incorporated herein by reference for all purposes.

FIELD OF THE INVENTION

The present invention relates to biometric sensors. More particularly, the present invention relates to a biometric sensor and sensor panel, a method for detecting a biometric pattern using the biometric sensor panel, and a method for manufacturing the biometric sensor and sensor panel.

BACKGROUND OF THE INVENTION

Today, the need for correctly verifying an individual's identity has become essential both to prevent identification (ID)-based fraud in our new age of electronic information and payments as well as to allow or prevent physical and/or electronic access in numerous situations to ensure and maintain the integrity of premises and/or systems. For example, "ID-based fraud" includes such items as improper payment card usage, theft and misappropriation of identity information and even the use of false credentials. Examples of "access" include access to specific information, services, and/or communication facilities, use of specific devices or equipment such as computers, mobile phones, handheld devices, automobiles, or machinery, physical access to a restricted area or premises, or even entry into a country as with a passport. Biometric information or signatures, such as a fingerprint pattern, a voiceprint pattern, physical appearance (a face, an ear, an iris, a retina, and the like, of a person), biological assay, and the like, can be used as a more reliable, secure, and convenient method for verifying a person's identity compared with the traditional method of password-based verification.

Among biometric signatures, fingerprints have been traditionally one of the most frequently used and various types of fingerprint sensors have been developed. For example, a capacitive fingerprint sensor typically measures the electrical capacitance between a number of sensing elements arranged in an array and the fingerprint contour, i.e., ridges and valleys of the finger skin. However, such capacitive fingerprint sensors are typically affected by the condition of a finger, such as moisture and/or dirt on the finger. An optical, contactless-type fingerprint sensor is neither affected by finger condition (dry/humid) or smearing effect. However, optical fingerprint sensors typically require complex detection circuitry and extensive data processing for pattern recognition, they are not suitable for small portable devices with limited computational capacity, or "card" applications such as smart cards, credit cards, bank cards, driver's licenses, passports, and the like. In addition, the biometric sensor needs to be sufficiently small in size (i.e., thin and light), durable, and also cost effective in order to be implemented in such card applications. For example, the cost of conventional fingerprint sensors including a sensor array using standard CMOS technology would make it economically impractical at the present time to be implemented in such card applications.

BRIEF SUMMARY OF THE INVENTION

A biometric sensor panel includes (a) a first flexible substrate, (b) a plurality of first electrodes formed on the first flexible substrate, the first electrodes being arranged in a first direction, (c) a semiconductor layer formed on the first electrodes, (d) a second flexible substrate, (e) a plurality of second electrodes formed on the second flexible substrate, the second electrodes being arranged in a second direction crossing the first direction, and (f) a pressure sensitive conductive layer formed on the second electrodes, wherein the first and second flexible substrates face each other such that the semiconductor layer is in contact with the pressure sensitive conductive layer.

BRIEF DESCRIPTION OF THE DRAWINGS

The accompanying drawings, which are incorporated into and constitute a part of this specification, illustrate one or more embodiments of the present invention and, together with the detailed description, serve to explain the principles and implementations of the invention.

In the drawings:

FIG. 10 is a diagram schematically illustrating a biometric sensor in accordance with one embodiment of the present invention, including driver and detector circuits thereof.

DETAILED DESCRIPTION OF THE INVENTION

Embodiments of the present invention are described herein in the context of a biometric sensor, a sensor panel, a method for detecting a biometric pattern using the same, and method for manufacturing the same. Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Figure 1:
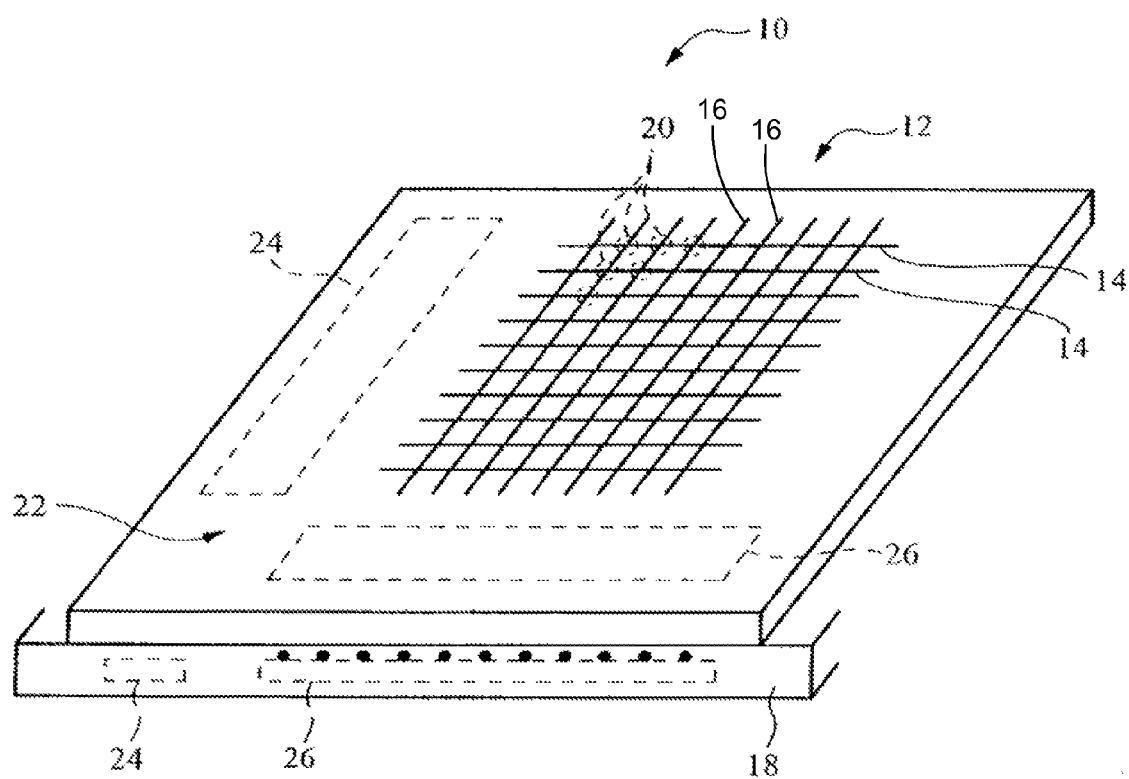
FIG. 1 is a perspective diagram schematically illustrating a general structure of a biometric sensor in accordance with one embodiment of the present invention.

FIG. 1 is a perspective diagram schematically illustrating a general structure of a biometric sensor 10 in accordance with one embodiment of the present invention. As shown in FIG. 1, a biometric sensor 10 includes a sensor panel 12 having a plurality of first electrodes (metal layer) 14 arranged in a first direction (for example, the X-direction) and a plurality of second electrodes (metal layer) 16 arranged in a second direction crossing the first direction (for example, the Y-direction). An intermediate layer (not shown in FIG. 1) is provided between the first electrodes 14 and the second electrodes 16. Each crossing of the first electrodes 14 and the second electrodes 16 forms a passive sensor element (or sensor cell) 20. That is, the sensor panel 12 has an array (matrix) of passive sensor elements 20. In accordance with a biometric pattern impressed thereon, each of the passive sensor elements 20 changes its electrical characteristics (conductivity) between the first electrode 14 and the second electrode 16.

Figure 2:
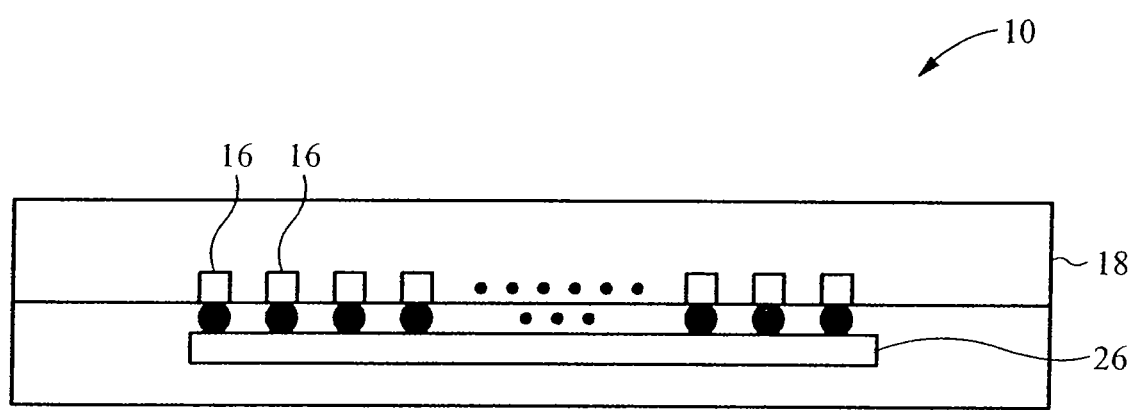
FIG. 2 is a cross-sectional diagram schematically illustrating a cross-sectional view of the second circuit connected to the second electrodes inside the base substrate, in accordance with one embodiment of the present invention.

A driver/detector part 22 of the biometric sensor 10 includes a first circuit 24 and a second circuit 26. The first circuit 24 is coupled to the first electrodes 14, and the second circuit 26 is coupled to the second electrodes 16. The first and second circuits 24 and 26 are adapted to detect changes in the conductive characteristic at each crossing (sensor element 20) caused by the biometric pattern impressed on the sensor panel 12. As shown in FIG. 1, the first electrodes 14, the second electrodes 16, the first circuit 24, and the second circuit 26 are embedded in a base substrate 18. The base substrate 18 may be made, for example, of an elastic material such as glass epoxy or bismaleimide-triazine (BT) resin. Other materials known to those of ordinary skill in the art may also be used. The first and second circuits 24 and 26 may be implemented in respective integrated circuit (IC) chips, and such IC chips are encapsulated in the base substrate 18 such that the surface of the base substrate 18 is flat and does not have any protruding portion. FIG. 2 is a cross-sectional diagram schematically illustrating a cross-sectional view of the second circuit 26 connected to the second electrodes 16 inside the base substrate 18, in accordance with one embodiment of the present invention.

Figure 3A:
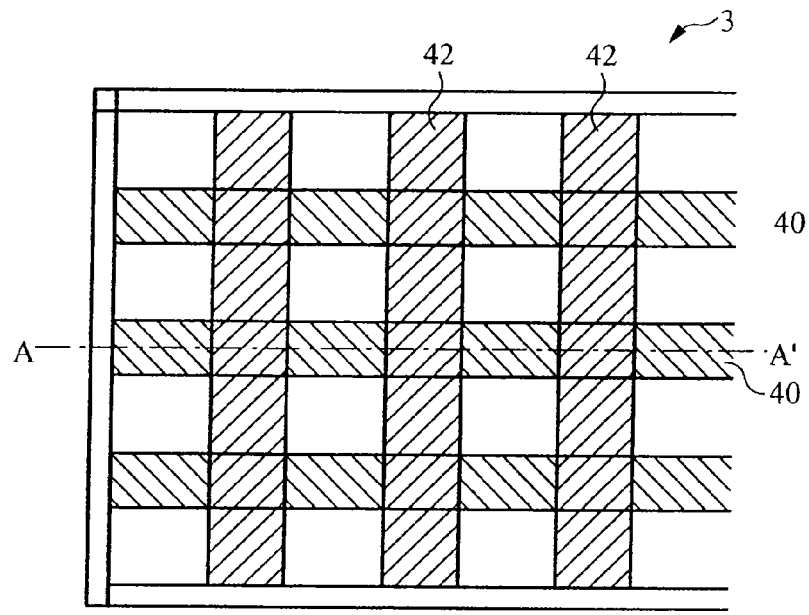
FIG. 3A is a diagram schematically illustrating a portion of a sensor panel forming part of a biometric sensor in accordance with one embodiment of the present invention.
Figure 3B:
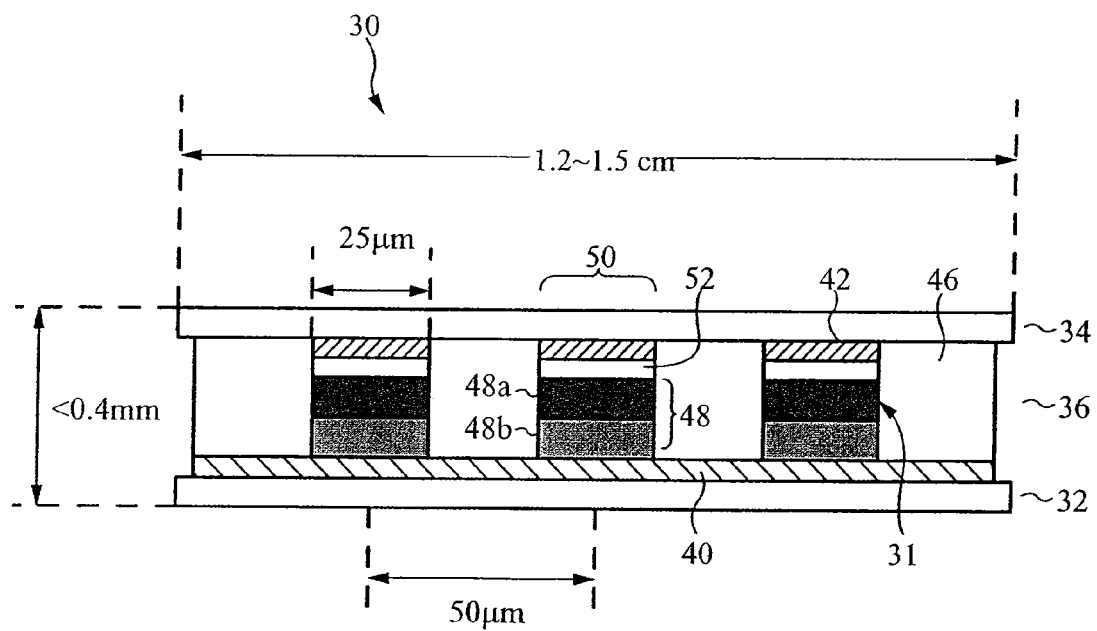
FIG. 3B is a cross-sectional diagram taken along line 3B-3B, schematically illustrating a cross-sectional view of the biometric sensor of FIG. 3A.

FIG. 3A is a diagram schematically illustrating a portion of a sensor panel forming part of a biometric sensor in accordance with one embodiment of the present invention. FIG. 3B is a cross-sectional diagram taken along line 3B-3B, schematically illustrating a cross-sectional view of the biometric sensor of FIG. 3A. Biometric sensor panel 30 includes a first flexible substrate 32, a second flexible substrate 34, and an intermediate layer 36 provided between the first substrate 32 and the second substrate 34. The first flexible substrate 32 has a plurality of first electrodes (metal layers) 40 formed thereon and arranged in a first direction (for example, the X-direction). Similarly, the second flexible substrate 34 has a plurality of second electrodes (metal layers) 42 formed thereon and arranged in a second direction (for example, the Y-direction). The first and second flexible substrate may be made of a plastic material, such as polyimide, polyethylenenapthalate (PEN), polyester (PET), polyethelenetherketone (PEEK), polycarbonate, and the like, or suitable substitutes.

The first and second electrodes 40 and 42 are also flexible. The first and second electrodes 40 and 42 may be made of metals such as Cu or Cu/Au. Indium tin oxide (ITO) may also be used for the first and/or second electrodes. The electrodes may, in one embodiment, have a thickness of about 3-5 μm, a width (w) of about 25 μm, and arranged with a pitch (P) of about 50 μm. The width (and length) of the sensor panel part may be about a half inch (or about 1.2-1.5 cm). The thickness (T) of the sensor panel may be less than 0.4 mm. However, these materials and numbers are by way of example and are not intended to be exhaustive or limiting in any way. It should also be noted that only three each of the first and second electrodes are illustrated in the drawings for simplicity.

As shown in FIG. 3B, the first electrodes 40 and the second electrodes 42 face each other via the intermediate layer 36. The intermediate layer 36 includes an insulation film (dry film) 46 and a flexible diode layer 48 provided in the insulation film 64 at each crossing portion of the first and second electrodes 40 and 42. For example, the insulation film 46 may be formed of a UV-setting resin or photo-polymerizing material (referred to as "photo-setting resin"). As shown in FIG. 3B, the insulation film (layer) has a via hole 31 between the first and second flexible substrate 32 and 34 at each crossing portion of the first and second electrodes 40 and 42. The diode layer 48 is provided on the first electrode 40 in each via hole 31, and a gap 52 is provided between the diode layer 48 and the second electrode 42 in each via hole 31. The gap 52 allows the second electrode 42 to be electrically connected to the diode layer 48 if the second flexible substrate 34 is depressed by a biometric pattern towards the first flexible substrate 32 at the corresponding crossing portion.

The diode layer 48 may be made of a polymer diode including a PN-junction, and formed by laminating a P-type polymer 48a and an N-type polymer 48b, as shown in FIG. 3B. For example, conjugated polymers such as Polyaniline-Dodecylbenzenesulfonic acid (Pani-DBSA), available as Panipol®, from Panipol Ltd., Finland, f.k.a. UNIAX Corporation, Neste Oy, Finland, which is a solution and melt processable polymer in the doped state, or Bayton P®(PEDOT-PPS), available from Bayer AG, Germany, which is a soluble polymer in the doped state, conductive polyaniline (ORMECON®), available from Ormecon AG, Germany, or polymer light emitting diodes (PLED) such as PEHP-PPV, available from UNIAX Corporation, USA, Cambridge Display Technology, England, Philips, The Netherlands, COVION, Germany, and the like, can be used to form the diode layer 48.

For P-type polymer 48a, P-type organic semiconductor materials, such as pentacene (of good hole mobility) or conductive polymer (of good hole mobility) may be used. For N-type polymer 48b, N-type organic semiconductors such as perfluorinated pentacene with electron-withdrawing elements attached at molecular terminals, and fullerene derivative ([6,6]-phenyl C61-butyric acid methyl ester, PCBM) may be used. Furthermore, fullerene (C60) of soccer ball-like construction is known to have the highest electron mobility despite its simple structure, and a synthesized fullerene derivative (C60-fused pyrrolidine-meta-C12 phenyl: C60MC 12) with 12-carbon alkyl chain incorporated to fullerene (C60), and the like, may be used. The diode layer 48 may also be a light emitting diode. If a light emitting diode is used for the diode layer 48, the sensor panel part may be part of, or used as, a display, by providing a driving circuit for the display function and using transparent materials above the intermediate layer 36.

Alternatively, the diode layer 48 may include a PIN junction, or may be a Schottky diode including a metal-semiconductor junction. P-type and/or N-type semiconducting polymers may be used for the PIN or Schottky diode in a similar manner as those described above. An insulating polymer layer may be formed between the P-type and N-type semiconducting polymer layer in order to form a PIN junction. Using Schottky diode requires only one polymer layer, and thus the structure of the sensor element can be very simple and made using a short process. The Schottky diode may include a junction between metal and a N-type polymer, P-type polymer, and/or I-type polymer. The metal may also be Indium Thin Oxide (ITO). Schottky diode also has other advantages such as fast switching speed, low forward voltage drop, and hot carrier. For example, if logic devices such as CMOS are used with the supply voltage Vcc of 3.3 volt, the threshold voltage Vth would be 1.6 volt. If driver logic is operated at 3.3 volt, the output voltage Vf of a PN polymer junction may be 2 volt, since regardless of the applied voltage, the output voltage Vf is always higher than Vth. However, in case of Schottky diode, the output voltage Vf may be 0.3-0.5 volt, which gives sufficient voltage for sensor elements.

At each crossing of the first electrode 40 and the second electrode 42 (i.e., the via hole 31), a passive sensor element 50 is formed. That is, the corresponding part of the first and second electrodes 40 and 42, the diode layer 48, and the gap 52 form a sensor element 50. The gap 52 may be an air gap, which prevents the second electrode 42 from coming into contact with the diode layer 48 when there is no deformation of the second flexible substrate 34 (i.e., no finger is placed on the sensor 30). Alternatively, the gap 52 may be formed of a reversible anisotropic conductive film (ACF), which conducts, only when pressed, in the direction of the pressure. The gap 52 may also be made of a elastic resin layer containing conductive particles, which conducts when it is depressed and returns to non-conductive when the pressure is removed. Since the diode layer 48 in each crossing (i.e., the sensor element 50) is isolated each other by the insulation film 46, conductivity of the gap material need not be isotropic. In either case, the gap 52 provides electrical connection between the second electrode 42 and the diode layer 48 only when the corresponding sensor element 50 is depressed by a biometric pattern.

The gap 52 (coupled with the diode layer 48 and the second electrode 42) operates as a switching element which conducts (ON state) in accordance with the biometric pattern. The diode layer 48 provides an ON current in a specific direction (from the second electrode 42 to the first electrode 40 in this example), which prevents unwanted current flows and cross talks between sensor elements 50. The amount of the gap 52 may be in a range of 5 to 10 µm. The gap 52 may also be properly selected in accordance with the flexibility and/or the amount of the deformation of the second flexible substrate 34. If the gap 52 is an ACF layer or the pressure-conductive layer, the amount of the gap 52 may also depend on the pressure necessary to make the gap 52 conductive.

Figure 4A:
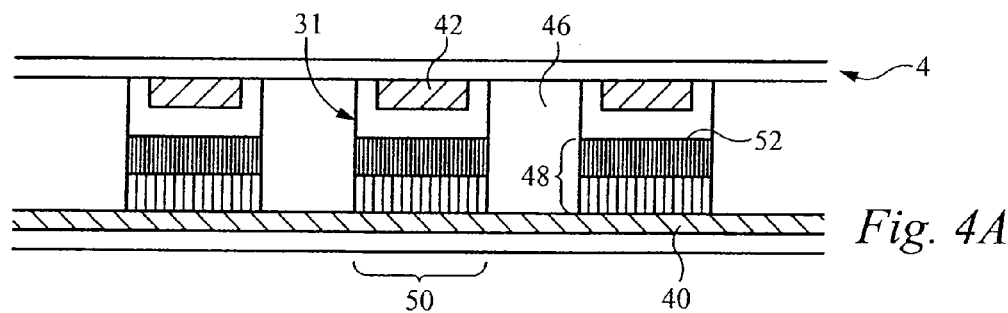
FIGS. 4A through 4D are cross-sectional diagrams schematically illustrating examples of the configuration of the sensor elements formed at crossings of the first and second electrodes in accordance with various embodiments of the present invention.
Figure 4B:
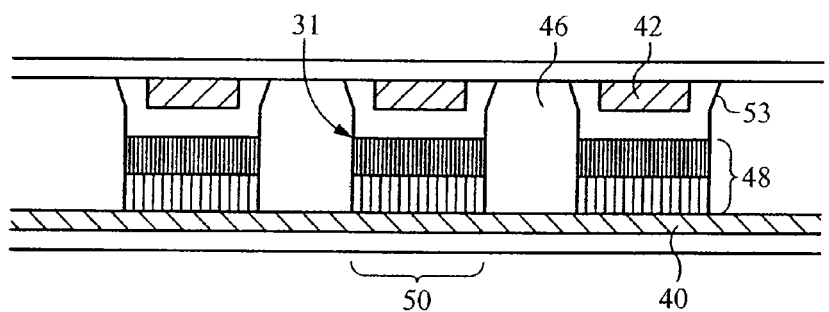
Figure 4C:
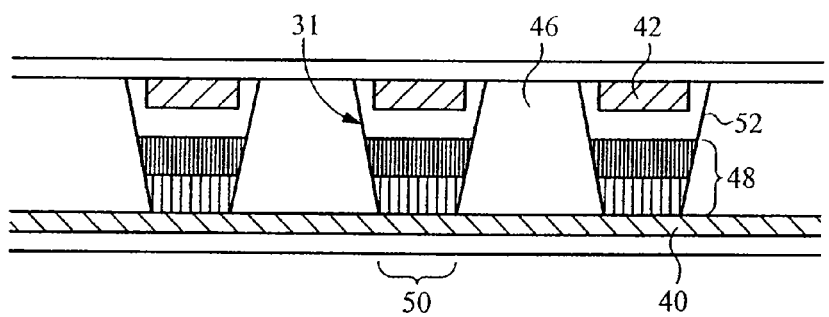
Figure 4D:
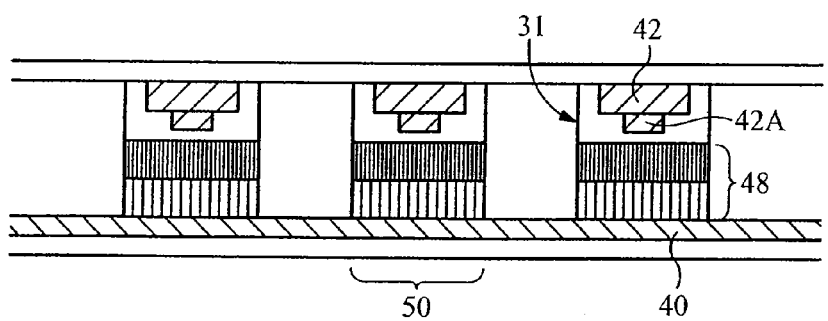

FIGS. 4A through 4D are cross-sectional diagrams schematically illustrating examples of the configuration of the sensor elements 50 formed at crossings of the first and second electrodes 40 and 42 in accordance with various embodiments of the present invention. As shown in FIG. 4A, the width of the second electrode 42 may be slightly narrower than the width of the diode layer 48 (or the width of the via hole 31) such that the second electrode 42 moves easily toward the diode layer 48 to come into contact therewith when the corresponding crossing portion (sensor element 50) is depressed by a biometric pattern. The wall 53 of the vial hole 31 in the insulation film 46 may be partially or entirely tapered, as shown in FIGS. 4B and 4C, respectively, such that the opening of the via hole 31 for receiving the second electrode 42 is slightly greater than the width of the second electrode 42. In addition, a conductive bump 42a may be provided on the second electrode 42 at each crossing portion (into the via hole 31) so as to provide better electric connection when the second electrode 42 comes into contact with the diode layer 48.

Figure 5:
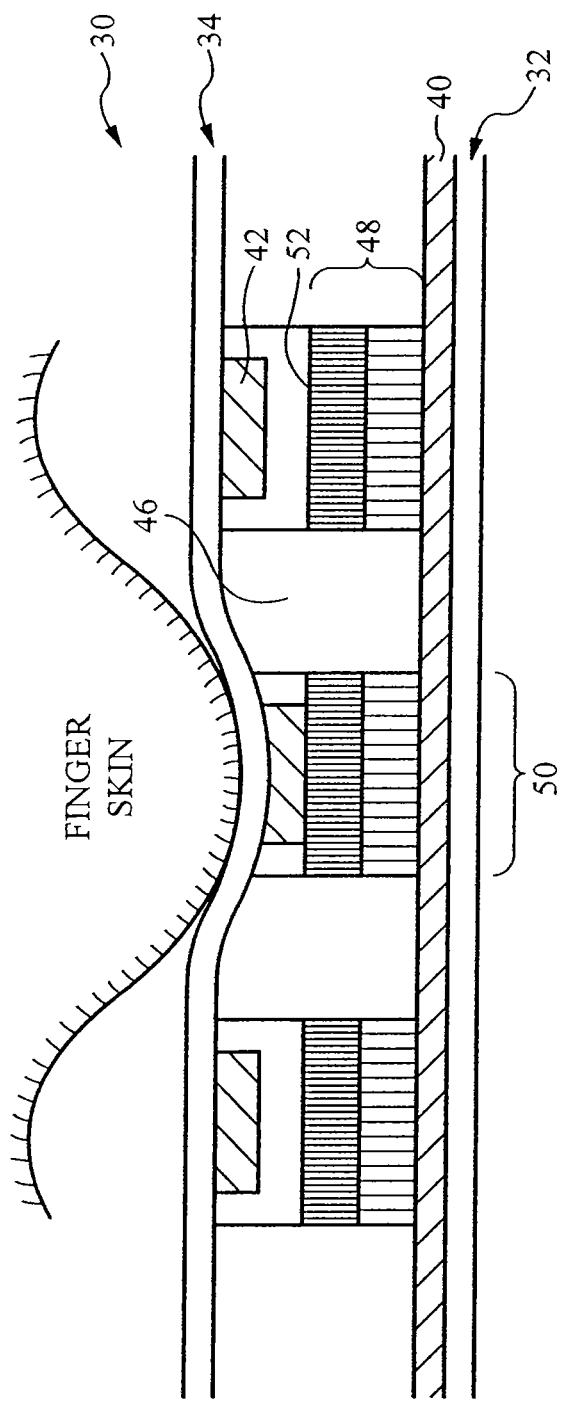
FIG. 5 is a cross-sectional diagram schematically illustrating a portion of a sensor panel part of a biometric sensor being touched by a finger in accordance with one embodiment of the present invention.

FIG. 5 is a cross-sectional diagram schematically illustrating a portion of a sensor panel part of a biometric sensor being touched by a finger in accordance with one embodiment of the present invention. As shown in FIG. 5, the second substrate 34 is deformed in accordance with the fingerprint pattern. A ridge of the fingerprint pattern depresses the second substrate 34 towards the first substrate 32 such that the corresponding second electrode 42 moves downward until it comes into contact with the diode layer 48 (in the case of an air gap 52). Thus, the sensor elements 50 which are depressed by the ridge of the fingerprint pattern provide an electrical connection between the first and second electrodes 32 and 34 via the diode layer 48 (ON state), while other sensor elements 50 which are not depressed by the fingerprint pattern are in a OFF state.

Figure 6:
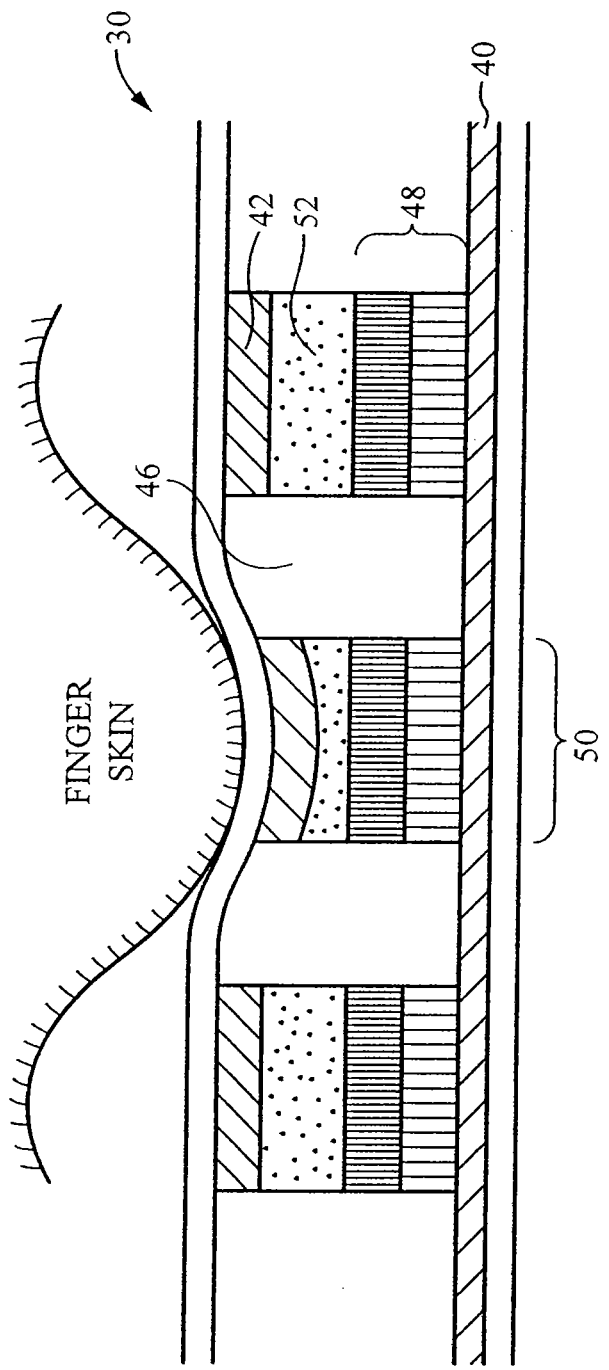
FIG. 6 is a cross-sectional diagram schematically illustrating a portion of a sensor panel part of a biometric sensor being touched by a finger in which the gap is made of an ACF or a pressure-sensitive (conductive) resistive film, in accordance with one embodiment of the present invention.

FIG. 6 is a cross-sectional diagram schematically illustrating a portion of a sensor panel part of a biometric sensor being touched by a finger in which the gap is made of an ACF or a pressure-sensitive (conductive) resistive film, in accordance with one embodiment of the present invention. When a ridge of the fingerprint pattern depresses the second substrate 34 towards the first substrate 32 such that the corresponding second electrode 42 moves downward, the gap layer (an ACF or resistive film) is pressed and becomes conductive, providing an electrical connection between the second electrode 42 and diode layer 48. Such a pressure-sensitive resistive film may be an elastic material layer containing conductive particle or metallization formed of one or more materials selected from the group consisting of: Cr/Ni, Cr/Ni/Au, Ti/Ni, Ti/Ni/Au, Cr/Cu, Cr/Cu/Au, Ti/Cu, Ti/Cu/Au, Cr/Al, Cr/Al/Au, Ti/Al, Ti/Al/Au, Cr/Ag, Cr/Ag/Au, Ti/Ag, Ti/Ag/Au, Al, Au, Ni, and TiN.

Figure 7:
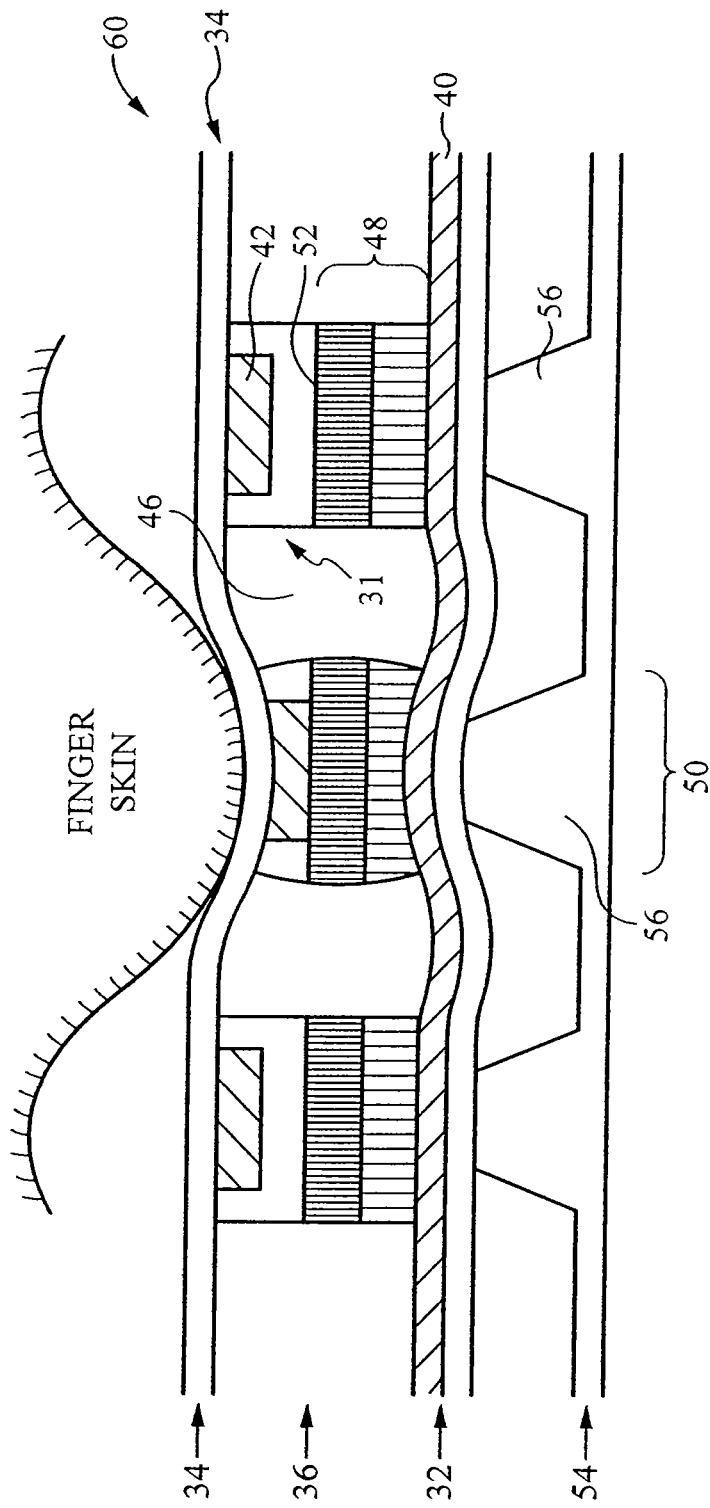
FIG. 7 is a cross-sectional diagram schematically illustrating a portion of a sensor panel part of a biometric sensor being touched by a finger and having lower support bumps provided under the first flexible substrate in accordance with one embodiment of the present invention.

FIG. 7 is a cross-sectional diagram schematically illustrating a portion of a sensor panel part of a biometric sensor being touched by a finger and having lower support bumps provided under the first flexible substrate in accordance with one embodiment of the present invention. The biometric sensor 60 includes, similarly to the biometric sensor panel 30, a first flexible substrate 32, a plurality of first electrodes 40 formed on the first flexible substrate 32 and arranged in a first direction, a second flexible substrate 34, a plurality of second electrodes 42 formed on the second flexible substrate 34 and arranged in a second direction, and an intermediate layer 36 provided between the first flexible substrate 32 and the second flexible substrate 34. Also similarly to the biometric sensor panel 30, the intermediate layer 36 includes an insulation film 46, and a diode layer 48 and a gap 52 provided in each via hole 31 at each of crossing portion of the first and second electrodes 40 and 42. As shown in FIG. 7, the biometric sensor panel 60 further includes a back layer 54 having a plurality of lower support bumps 56 provided thereon. The back layer 54 contacts with the first flexible layer 32 via the plurality of lower support bumps 56 which are arranged such that the lower support bumps 56 are aligned with the sensor elements 50 (i.e., corresponding crossings of the first and second electrodes 40 and 42). When the second flexible substrate 34 is depressed by a biometric pattern and the corresponding crossing portion is pushed down, as shown in FIG. 7, the lower support bump 56 underneath the first substrate 32 pushes up the first electrode 40 towards the second electrode 42, providing better a physical and electrical contact between the second electrode 42 and the diode layer 48 (for an air gap), or providing a greater pressure for conductivity (for an ACF or resistive film gap: not shown in FIG. 7).

Figure 8:
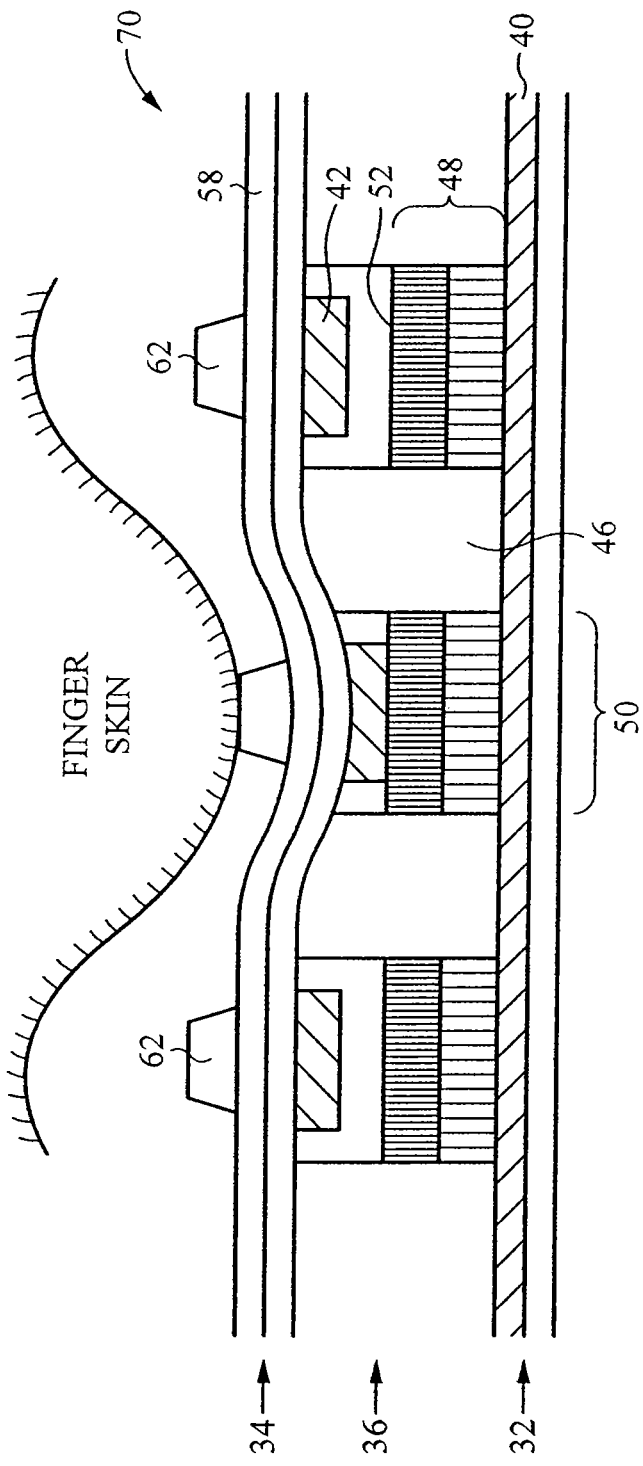
FIG. 8 is a cross-sectional diagram schematically illustrating a portion of a sensor panel part of a biometric sensor being touched by a finger and having a flexible protective layer including tactile location bumps formed on the second flexible substrate, in accordance with one embodiment of the present invention.

FIG. 8 is a cross-sectional diagram schematically illustrating a portion of a sensor panel part of a biometric sensor being touched by a finger and having a flexible protective layer including tactile location bumps formed on the second flexible substrate, in accordance with one embodiment of the present invention. As shown in FIG. 8, the protective layer 58 protects the biometric sensor panel 70 from unwanted mechanical or physical force. Furthermore, a plurality of tactile location bumps 62 may be provided on the protective layer 58 at locations corresponding to the sensor elements 50 (i.e., crossings of the first and second electrodes 40 and 42). When touched by a finger, the tactile location bumps 62 provide more localized pressure on the sensor elements 50 such that the corresponding portion of the second substrate 34 is well deformed to make the second electrode 42 and the diode layer 48 come into good contact with each other.

Figure 9:
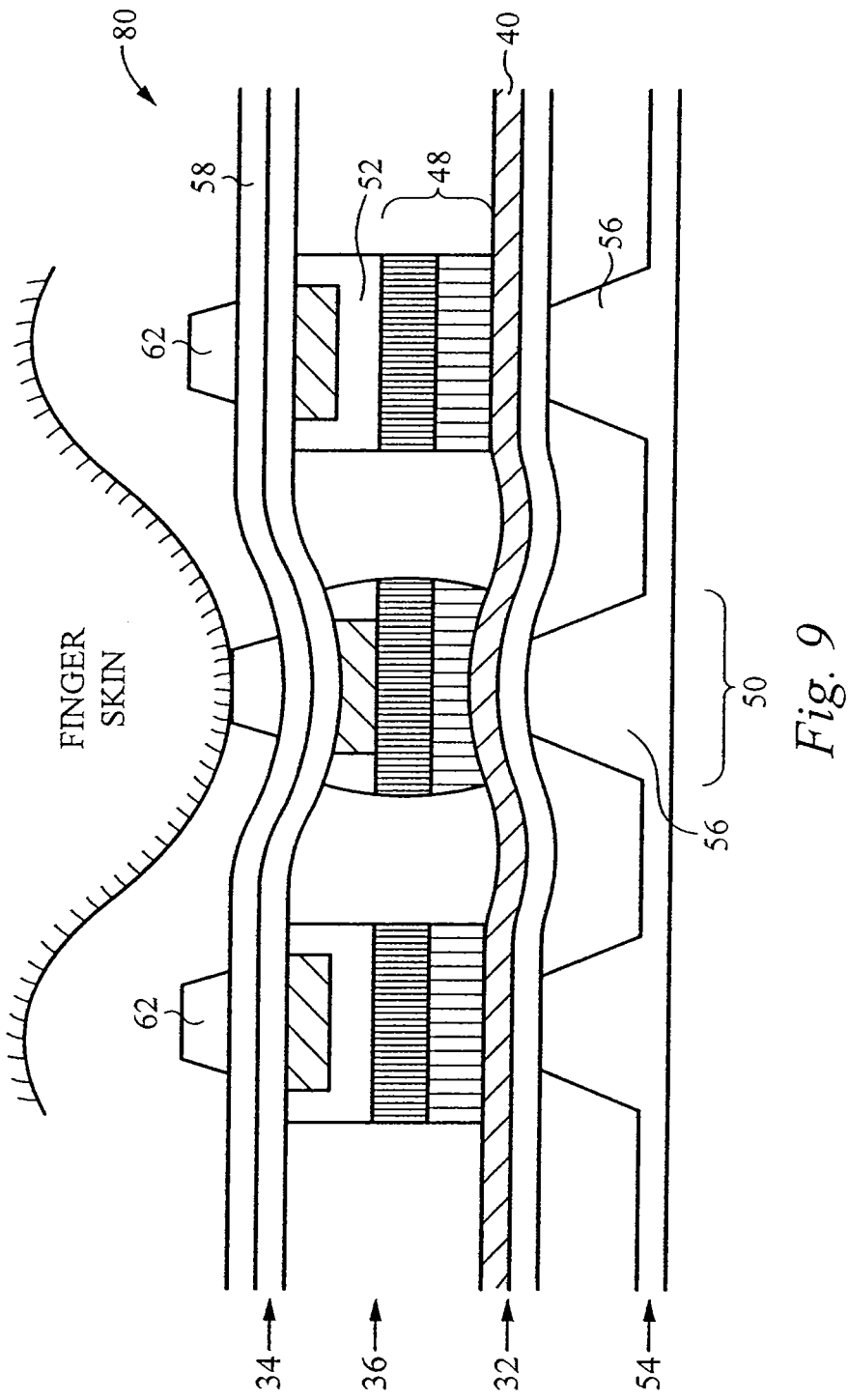
FIG. 9 is a diagram schematically illustrating a portion of a sensor panel part of a biometric sensor being touched by a finger and having both lower support bumps under the first flexible substrate and tactile location bumps on the protective layer of the second flexible substrate in accordance with one embodiment of the present invention.

FIG. 9 is a diagram schematically illustrating a portion of a sensor panel part of a biometric sensor being touched by a finger and having both lower support bumps under the first flexible substrate and tactile location bumps on the protective layer of the second flexible substrate in accordance with one embodiment of the present invention. As shown in FIG. 9, the tactile location bumps 62 can be used in combination with the lower support bumps 56 in the biometric sensor panel 80. It should be noted that FIGS. 7 through 9 illustrate biometric sensors having an air gap in each sensor element 50, these embodiments also apply to biometric sensors having an ACF or resistive film gap.

FIG. 10 is a diagram schematically illustrating a biometric sensor 100 in accordance with one embodiment of the present invention, including driver and detector circuits thereof. The biometric sensor 100 may use as the sensor panel 102 any one of the biometric sensor panels 10, 30, 60, 70, and 80 described above. The sensor panel 102 includes the first electrodes 104 arranged in a first (X) direction and the second electrodes 106 arranged in the second (Y) direction. The intermediate layer is not shown in FIG. 10. The first circuit 114 is coupled to the first electrodes 104, and the second driver circuit 116 is coupled to the second electrodes 106. The first and second circuits 114 and 116 are adapted to drive the corresponding electrodes and detect changes in the conductive characteristic (ON-OFF state of each of the sensor element) at each crossing caused by the biometric pattern impressed on the sensor panel 102.

For example, as shown in FIG. 10, suppose the sensor elements at the crossings $(X_2, Y_2), (X_3, Y_2), (X_3, Y_3)$, and $(X_4, Y_4)$ are depressed by a fingerprint pattern, which are indicated by "x". At these crossings, the first and second electrodes of the sensor element are electrically connected (i.e., in the ON state), and other sensor elements are in the OFF state. When detecting the fingerprint pattern, the second electrodes 106 are driven sequentially by the second circuit 116 using a second pulse signal 120 (pulse width T), and the first electrodes 104 are driven (or sensed) sequentially by the first circuit 114 using a first pulse signal 118 (pulse width t) within the pulse width T for each of the second electrodes 106 being driven.

Figure 11A:
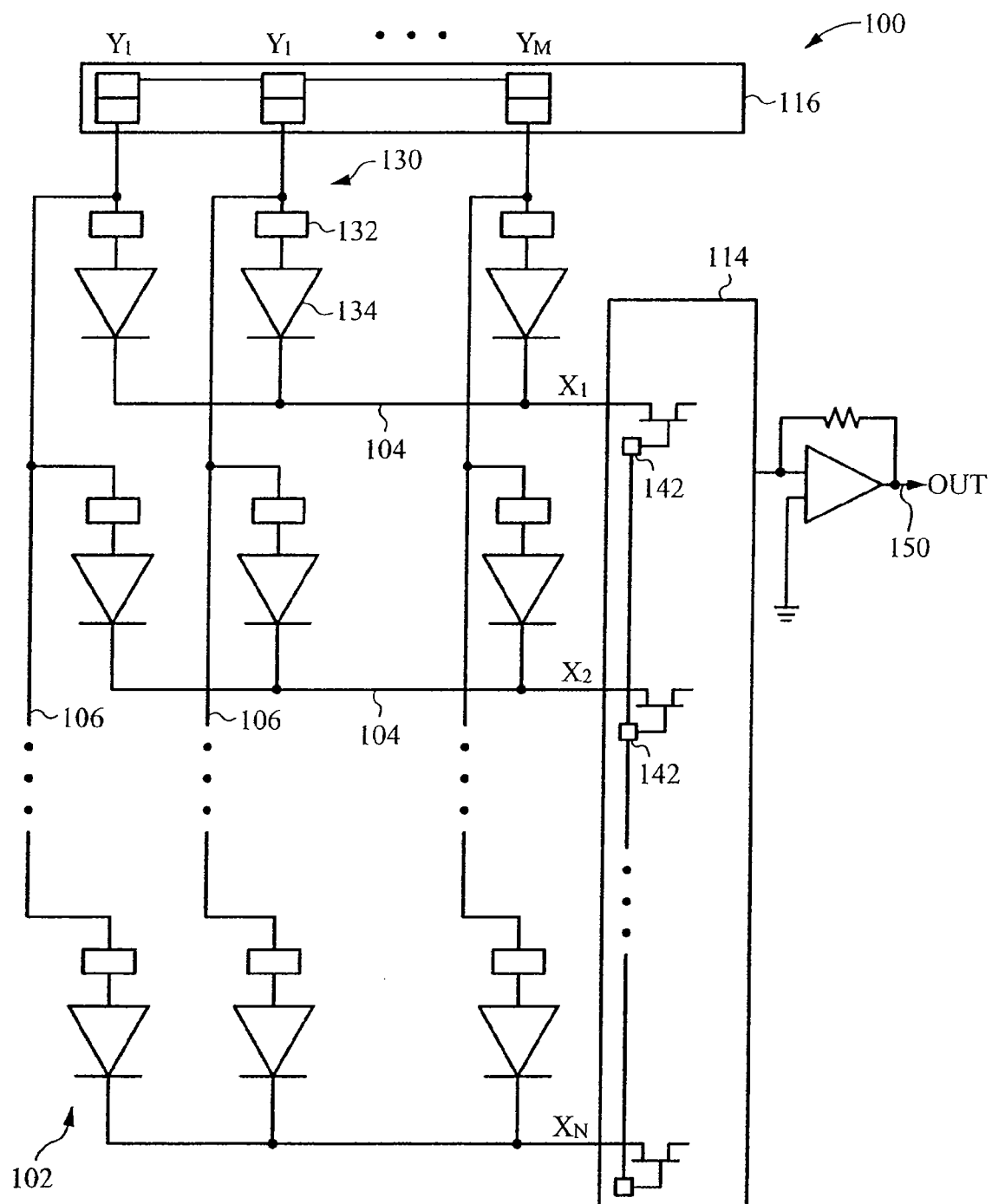
FIG. 11A is an electrical schematic diagram illustrating an example of an equivalent electrical circuit of the biometric sensor, in accordance with one embodiment of the present invention.

FIG. 11A is an electrical schematic diagram illustrating an example of an equivalent electrical circuit of the biometric sensor 100, in accordance with one embodiment of the present invention. The driver circuit 116 for the second electrodes may be a voltage driver including a transistor array or switch array adapted to sequentially apply a predetermined driving signal to the second electrodes. The driving (sensing) circuit 114 for the first electrodes may be a multiplexer using switching elements 142 for sequentially activating/selecting the first electrodes 104. The selected first electrode 104 is connected to the output 150 through an op-amp. Each sensor element 130 equivalently includes a switching element 132 and a diode 134. The switching element 132 turns ON if the corresponding sensor element 130 is being depressed by a biometric pattern, and otherwise remains OFF state. Thus, when a driving signal 120 is applied from the driving circuit 116, for example, to the second electrode $Y_1$, the outputs from the sensor elements 130 coupled to the second electrode $Y_i$ appear on the corresponding first electrodes $X_n$ ($1<n<N$) for the time period of T. The outputs are depending on the ON/OFF state of the sensor elements 130. Then, the electric signals on the first electrodes $X_i$ through $X_N$ are sequentially read out and multiplexed at the timing of pulse signal t. The multiplexed signal is output as a biometric (fingerprint) pattern signal (OUT) 150. Only ON-state sensor elements 130 generate an output pulse. The output pulse (ON state) may be set a logic High (1) and the no-pulse (OFF state) as logic Low (0). Then, in the next cycle of the driving pulse signal T, the next (second) electrode $Y_2$ is driven and the outputs from the sensor elements 130 coupled to the second electrode $Y_2$ are read out in a similar manner.

Figure 11B:
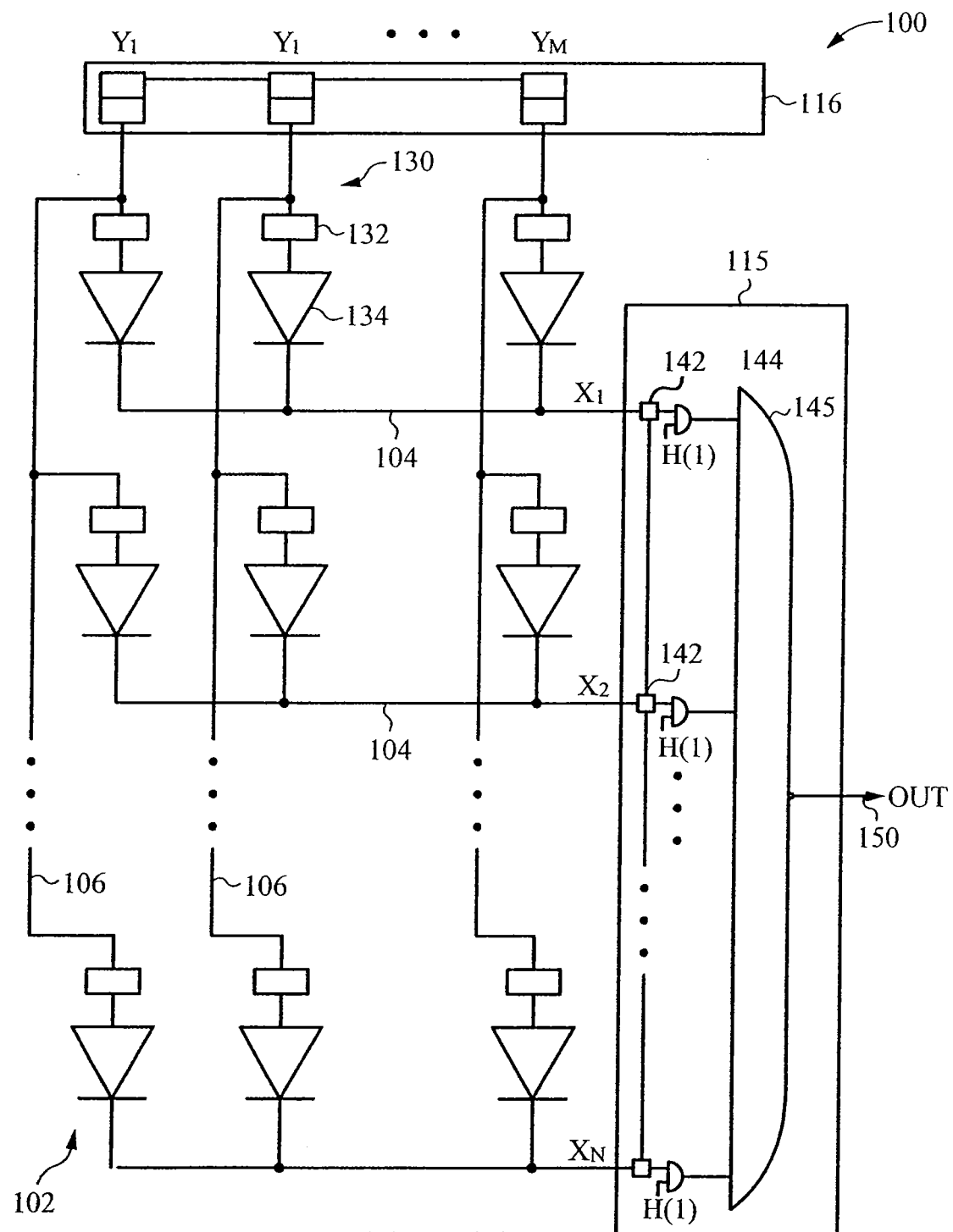
FIG. 11B is an electrical schematic diagram illustrating another example of an equivalent electrical circuit of the biometric sensor, in accordance with one embodiment of the present invention.

FIG. 11B is an electrical schematic diagram illustrating another example of an equivalent electrical circuit of the biometric sensor 100, in accordance with one embodiment of the present invention. In this example, a driving/sensing circuit 115 coupled to the first electrodes is implemented using logic gate arrays. Since outputs onto the first electrodes 104 are either logic High or Low, the signal on the first electrodes 104 may be detected using logic gates 144 (such as NAND gates, as shown in FIG. 11B), by sequentially selecting (at timing t) the first electrodes using the switching element 142. In this example, since the output of the NAND gate 144 of the first electrode which is unselected or which is connected to a OFF state sensor element is logic High (1), the output signal 150 becomes logic High only when the selected first electrode 104 is coupled to a ON-state sensor element. The switching element 142 may be provided at each output of the logic gate 144 instead of the input thereof.

Figure 12:
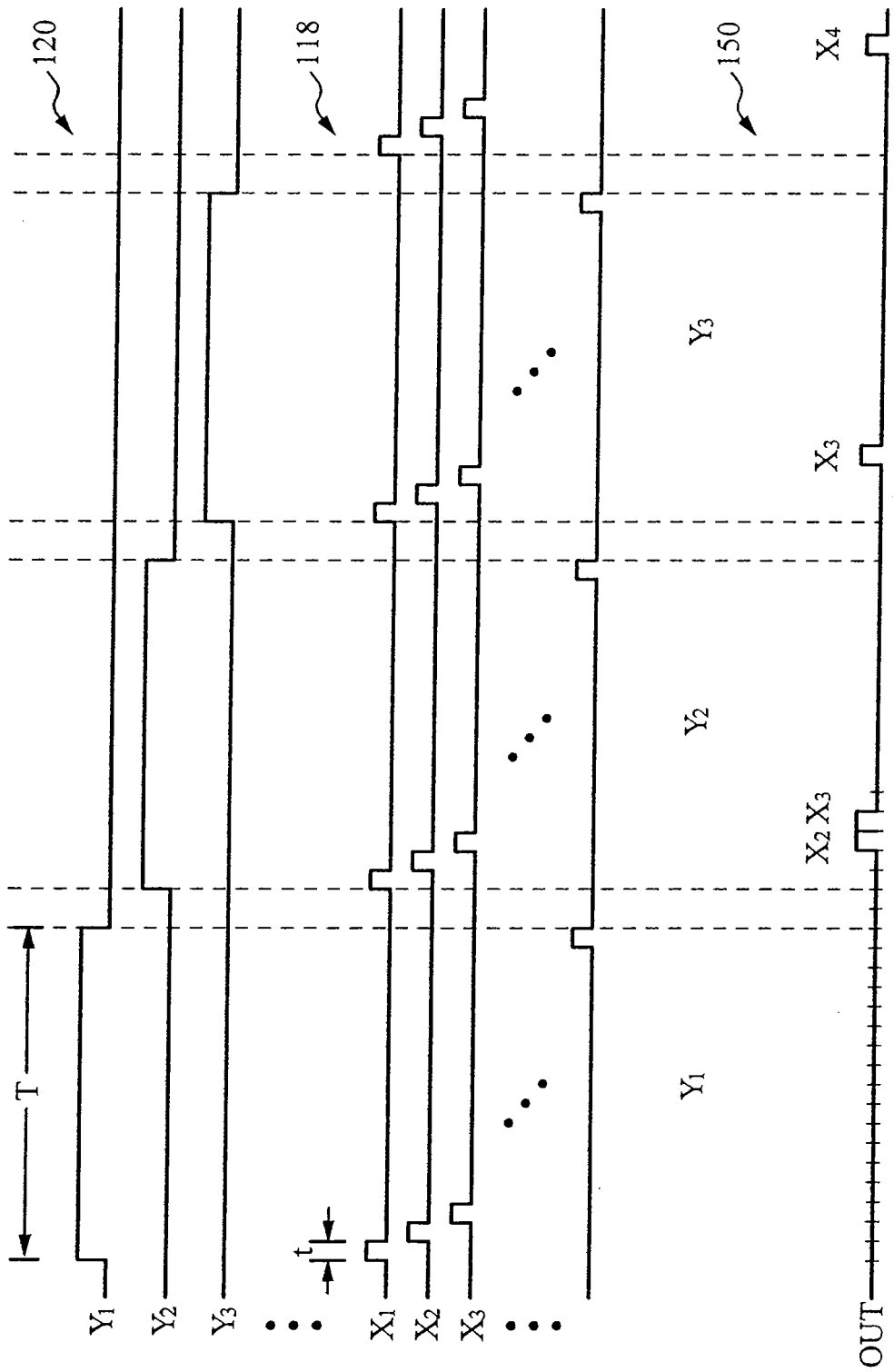
FIG. 12 is a timing chart schematically illustrating an example of first and second driving signals, and an output biometric pattern signal in driving and sensing circuits in accordance with one embodiment of the present invention.

FIG. 12 is a timing chart schematically illustrating an example of first and second driving signals, and an output biometric pattern signal in driving and sensing circuits in accordance with one embodiment of the present invention. As shown in FIG. 12, the second driving signal (e.g., a constant current signal) 120 is sequentially applied to the second electrodes (denoted as $Y_1, Y_2, \ldots, Y_M$ in FIGS. 11A and 11B) at the timing of the pulse signal T by the operation of the shift registers/latch. The first driving/sensing signal 118 is then sequentially applied (during the time period of T) to the first electrodes (denoted as $X_i, X_2, \ldots$ in FIGS. 11A and 11B) by the operation of the shift registers 142 such that the outputs from the corresponding sensor elements 130 are sequentially read out at the timing of the pulse signal t such that all of the first electrodes 104 are scanned with respect to each of the second electrodes 106.

In this example, as shown in FIG. 12, the output biometric pattern signal 150 has pulses corresponding to the depressed sensor elements 130 at the crossings of $(X_2, Y_2), (X_3, Y_2), (X_3, Y_3)$, and $(X_4, Y_4)$. It should be noted that the output biometric pattern signal 150 is in the form of pulse signal, and thus may be digitally processed without using an analog-digital converter, for authentication, authorization, and/or identification purpose, for example.

Figure 13:
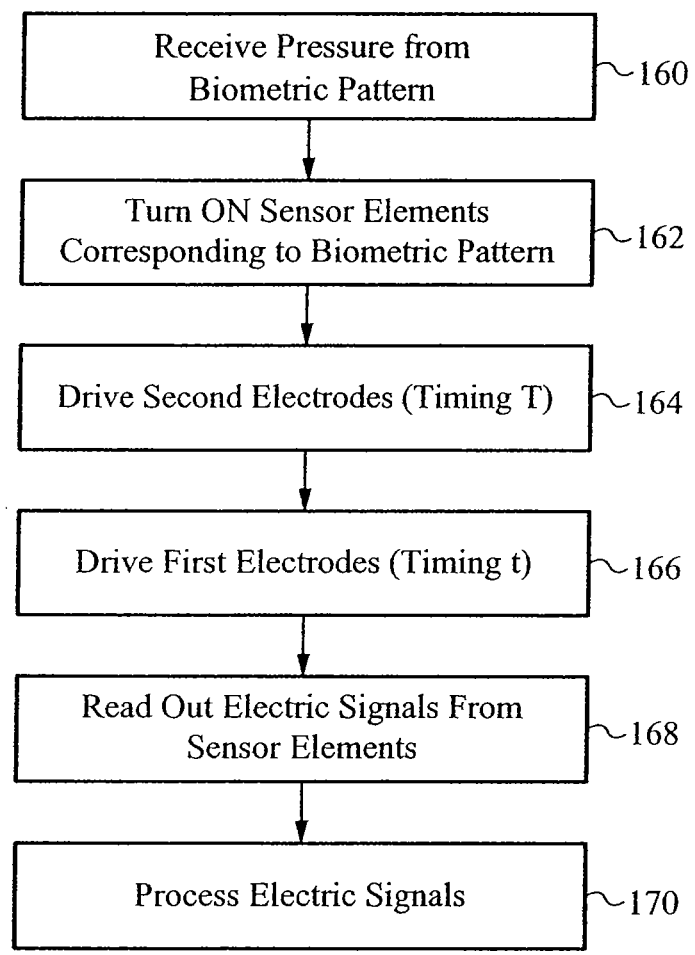
FIG. 13 is a process flow diagram schematically illustrating a method for detecting a biometric pattern using a biometric sensor panel, in accordance with one embodiment of the present invention.

FIG. 13 is a process flow diagram schematically illustrating a method for detecting a biometric pattern using a biometric sensor panel, in accordance with one embodiment of the present invention. The biometric sensor panel may be any one of sensor panels 10, 30, 60, 70, and 80 described above.

As shown in FIG. 13, a pressure from a biometric pattern is received on the second flexible substrate (160). The second flexible substrate deforms in accordance with the biometric pattern such that the second electrode and the diode layer are electrically connected via the gap in the sensor elements which are depressed by the biometric pattern. That is, the sensor elements corresponding to the biometric pattern are turned into the ON state (162). The plurality of second electrodes are driven (selected) in accordance with a timing (T) (164), and the plurality of first electrodes are driven (selected) in accordance with a timing (t) for each of the plurality of first electrodes which is being driven (166). The electric signals are read out from each of the sensor element through the first electrodes (168). The read-out signals are processed by a processor so as to compare and detect matching with reference data of the biometric pattern (170) for identification, authentication, and/or authorization purposes.

It should be noted that, although the driving signals are applied from the second electrodes and the outputs of the sensor elements are sensed through the first electrodes in the above-described embodiments, the driving signals may be applied from the first electrodes and the outputs of the sensor elements are sensed through the second electrodes by providing adequate driving/sensing circuits for the first and second electrodes.

Figure 14A:
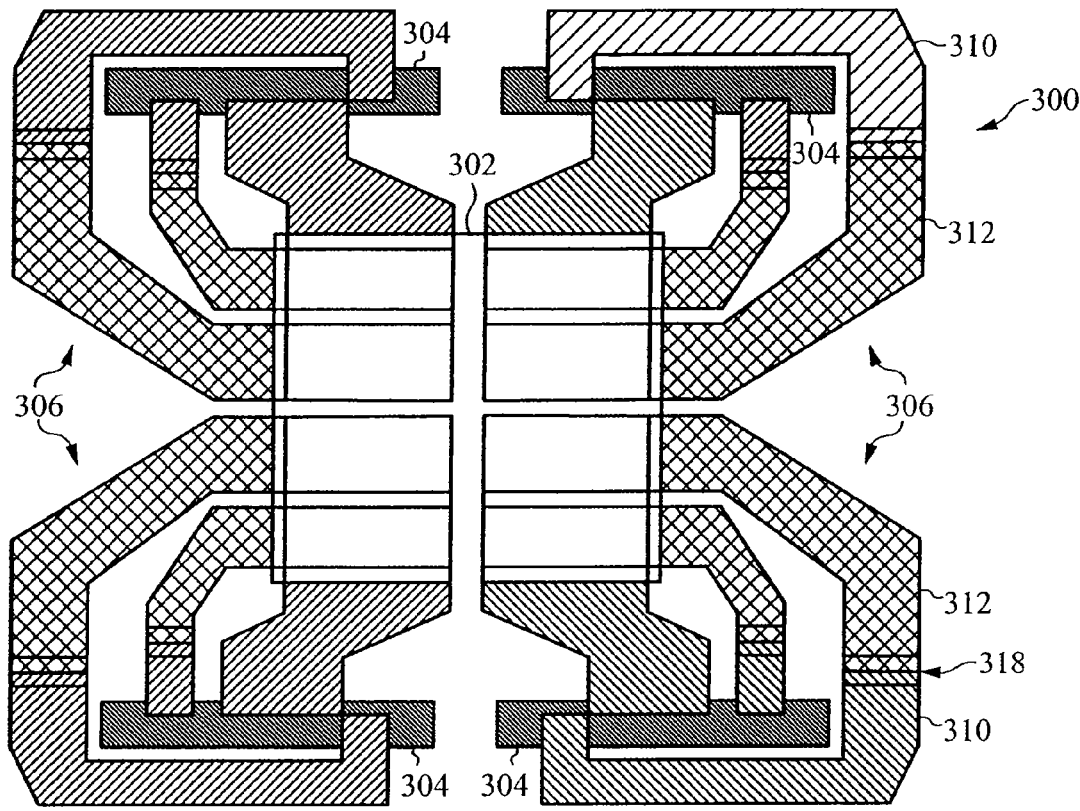
FIG. 14A is a top plan view diagram illustrating a biometric sensor implemented in a substrate in accordance with one embodiment of the present invention.
Figure 14B:
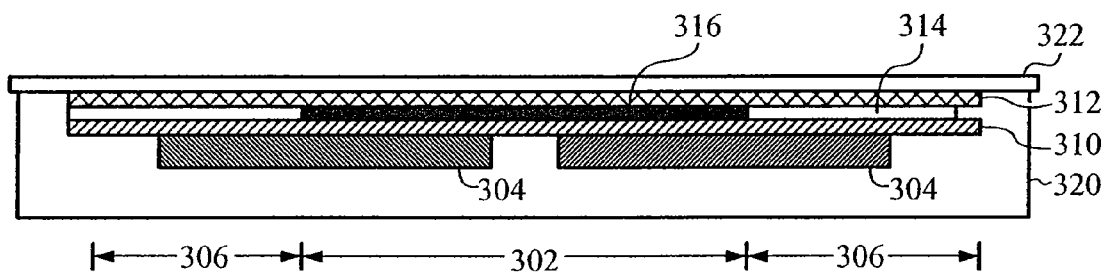
FIG. 14B is a cross-sectional view taken along line 14B-14B of FIG. 14A illustrating a cross-sectional view of a portion of the biometric sensor shown in FIG. 14A.

FIG. 14A is a top plan view diagram illustrating a biometric sensor implemented in a substrate in accordance with one embodiment of the present invention. FIG. 14B is a cross-sectional view taken along line 14B-14B of FIG. 14A illustrating a cross-sectional view of a portion of the biometric sensor shown in FIG. 14A. The biometric sensor 300 may use the biometric sensor panel 30, 60, 70, 80, or 100 described above. The biometric sensor 300 includes a sensor panel 302, driver and detector circuits 304, and lead lines 306 coupling the sensor panel part 302 to the respective driver and detector circuits 304. Although the sensor panel 302 includes a first flexible substrate, a second flexible substrate, and an intermediate layer between the first and second flexible substrate, as described above, their details are not shown in FIGS. 14A and 14B. In this example, the sensor panel part 302 are divided in four (4) sections, and each section has its own driver and detector circuits 304 which include a first circuit for driving the first electrodes and a second circuit for driving the second electrodes. In addition, the second electrodes may be divided in two halves and each half can be driven in parallel, such that a slower clock can be used for scanning.

As shown in FIG. 14B, the first electrodes (X-lines) and the corresponding lead lines are implemented using a first conductive layer 310, and the second electrodes (Y-lines) and the corresponding lead lines are implemented using a second conductive layer 312. An insulator layer 314 is provided between the first and second conductive layers 310 and 312. The first and second conductive layers 310 and 312 are connected via respective connecting slits 318 (shown in FIG. 14A). An intermediate layer 316 in the sensor panel part 302 includes the insulation film and the diode layer provided therein (not shown). As shown in FIG. 14B, the sensor panel 302, the lead lines 306, and the driving/detector circuits 304 are embedded in a base substrate 320 which is made, for example, of molding plastic. Since the driving/detector circuits 304 are encapsulated in the base substrate, the surface of the biometric sensor 300 can be flat and thus suitable for card or passport applications. In addition, a protective layer 322 may be provided on the surface of the substrate 320 from which a finger touches the biometric sensor 300. It should be noted that although detailed structure is not shown in FIGS. 14A and 14B, the biometric sensor in the above-described embodiments can be mounted/embedded in a similar manner.

Figure 15A:
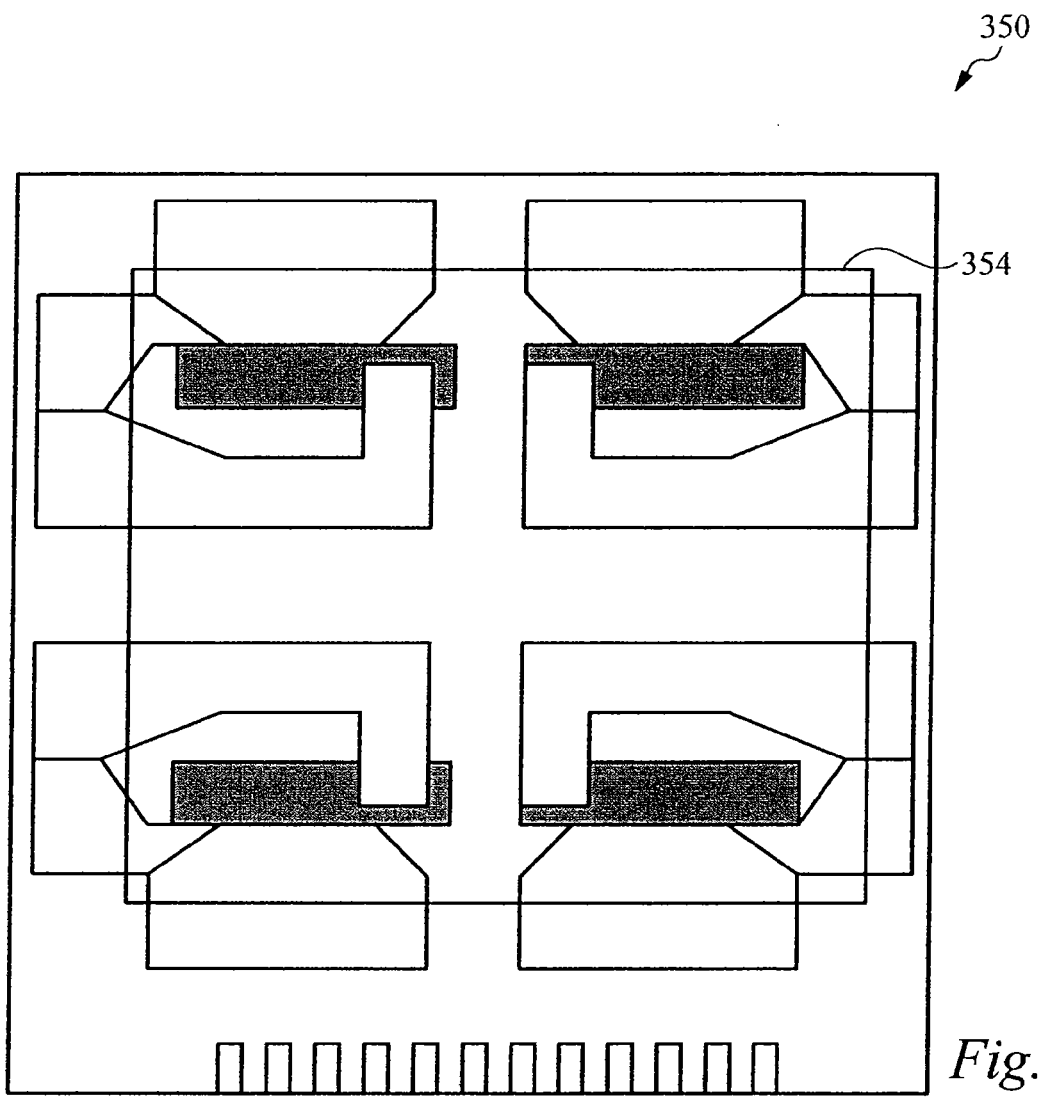
FIG. 15A is a top plan view diagram illustrating an example of encapsulated driver and detector circuits for a biometric sensor in accordance with one embodiment of the present invention.
Figure 15B:
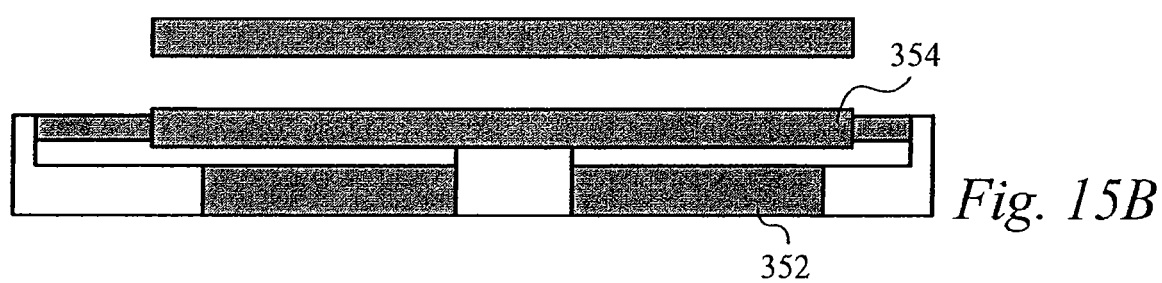
FIG. 15B is a cross-sectional view taken along line 15B-15B of FIG. 15A illustrating a cross-sectional view of a portion of the encapsulated driver and detector circuits of FIG. 15A.

FIG. 15A is a top plan view diagram illustrating an example of encapsulated driver and detector circuits for a biometric sensor 350 in accordance with one embodiment of the present invention. FIG. 15B is a cross-sectional view taken along line 15B-15B of FIG. 15A illustrating a cross-sectional view of a portion of the encapsulated driver and detector circuits of FIG. 15A. Compared with the embodiment shown FIGS. 14A and 14B, the driver and detector circuits 352 in this embodiment are encapsulated beneath the sensor panel part 354 so as to reduce the size of the biometric sensor 350.

Figure 16A:
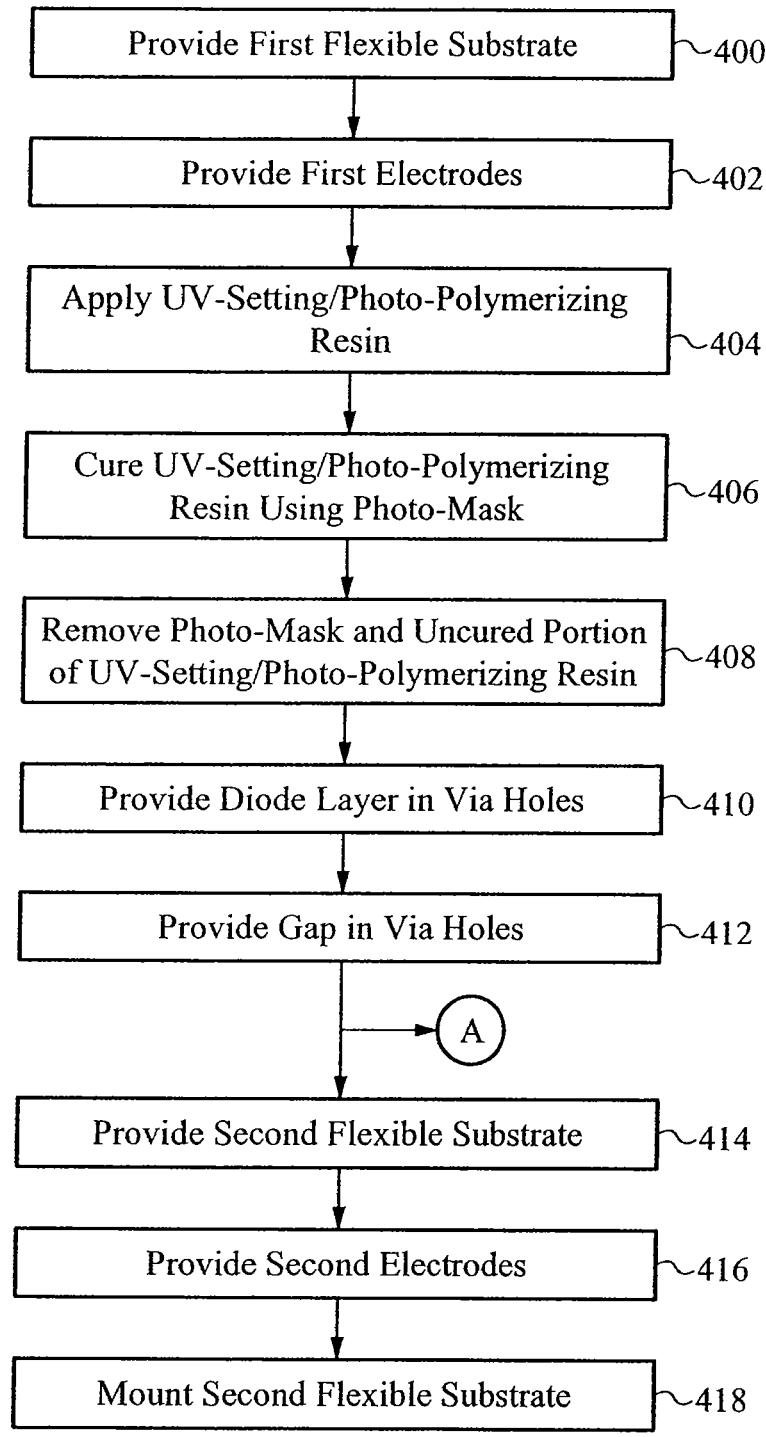
FIGS. 16A and 16B together form a process flow diagram schematically illustrating a method for manufacturing a biometric sensor panel having an array of sensor elements, in accordance with one embodiment of the present invention.
Figure 16B:
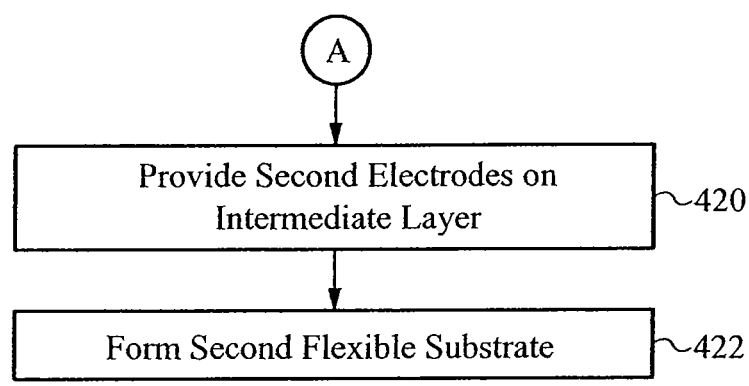

FIGS. 16A and 16B together form a process flow diagram schematically illustrating a method for manufacturing a biometric sensor panel having an array of sensor elements, in accordance with one embodiment of the present invention. As shown in FIG. 16A, a first flexible substrate is provided (400), and a plurality of first electrodes are formed on the first flexible substrate (402). The first electrodes are arranged in a first direction, and formed on the first flexible substrate. The first electrodes may be formed by depositing a conductive material layer (such as metal Cu, or Cu/Au film) on the first flexible substrate, and then patterning (for example, etching-off or stripped-off) the conductive material layer into the first electrodes. Alternatively, the first electrodes may be formed by (metalizing) plating a conductive material or metal into the first electrodes pattern. Any similar technology used to form metal lines on a printed circuit board (PCB) may be used. The first electrodes may also be formed using print-patterning technology (also referred to as digital lithography). The metal/conductor material may be directly printed where needed onto the first substrate so as to form the electrodes (metal layer lines).

An intermediate layer is then formed on the first flexible substrate which are provided with the first electrodes. A UV-setting or photo-polymerizing resin (photo-setting resin) is applied over the first flexible substrate provided with the plurality of first electrodes (404). The photo-setting resin is cured by irradiation of UV light (or non-UV light) using a photo-mask having a pattern for the sensor elements to be formed (406). The pattern of the photo-mask corresponds the crossings of the first and the second electrodes where the sensor elements are to be formed. That is, the resin in the location for the sensor elements is not cured. After curing the photo-setting resin, the photo-mask and the uncured portion of the photo-setting resin are removed (408). The uncured portion may be washed away from the first substrate. The resulting cured photo-setting resin layer forms an insulation layer having via holes to the first electrodes at locations for the sensor elements.

Then, a diode layer is provided in each of the via holes (410). The diode layer may be a lamination of a P-type and an N-type semiconducting polymers. For example, an N-type semiconducting polymer (melt or solution) is ink-jet printed into the via holes, or spin-coated on the insulation layer and doctor-bladed into the via holes. Also electrostatic coating may be used. When the N-type semiconducting polymer dries, its volume is reduced, leaving room for a P-type semiconducting polymer. Alternatively, the thickness of the insulation layer (sometimes referred to herein as "first insulation layer") may be set as the desired thickness of the N-type semiconducting polymer layer, and then a second insulation layer may be formed on top of the first insulation layer in order to provide an additional via hole depth for the P-type semiconducting polymer layer and the gap layer. For example, a second photo-setting resin may be applied over the insulation layer on the first flexible substrate, the second photo-setting resin is cured by irradiation of light using a photo-mask having the same pattern for the sensor elements to be formed, and then the photo-mask and the uncured portion of the second photo-setting resin are removed. The cured second photo-setting resin forms the second insulation layer having via holes connected to the respective via holes of the first insulation layer.

The P-type semiconducting polymer is then ink jet printed, or spin-coated and doctor-bladed into the via holes in a similar manner as the N-type semiconducting material. The laminated N and P-type polymer layers form a P-N junction in each via hole of the insulation layer. A gap is also provided above the diode layer in each via holes (412). The gap may be an air gap, or may be a gap layer made of an a reversible anisotropic conductive film (ACF) or a pressure-sensitive elastic resistive film. If the gap layer is to be made of an ACF or a pressure-sensitive elastic resistive film, such a film material may be deposited and patterned, or may be ink-jet printed or doctor bladed onto the diode layer in each via hole. A third insulation layer may be formed on the second or first insulation layer in order to provide the gap, the space for the gap layer, and/or the space for the second electrode to be formed, in a similar manner as that for the second insulation layer.

The thickness of the insulation layer, and the amount of the P-type and N-type semiconducting polymer to be provided into the via holes may be determined based on the desirable thickness or space of the gap. By controlling the thickness of the insulation resin layer and the diode layer to be formed in the via holes, a desired amount of space for the gap and/or the second electrode to be formed above the diode layer can be provided. Also, a PIN junction, or a metal-semiconductor junction can be formed as the diode layer in a similar manner as described above.

A second flexible substrate is also provided (414), and a plurality of second electrodes on the second flexible substrate (416) in a similar manner as the first electrode. The second electrodes are arranged in a second direction crossing the first direction. A plurality of bumps may be provided on the second electrodes (see FIG. 4D). The second flexible substrate thus provided with the second electrodes is mounted on the intermediate layer such that the second electrodes face the first electrode via the intermediate layer, and the first and second electrodes crossing each other at the locations of the sensor elements (i.e., at the via holes) (418).

Alternatively, in the case where an ACF or a pressure-sensitive film is formed as the gap on each of the diode layer, the second electrode may be provided on the intermediate layer such that the second electrodes faces the first electrodes via the intermediate layer and the first and second electrodes crossing each other at the location of the sensor elements (420) as shown in FIG. 16B, and then the second flexible substrate if formed on the second electrodes, covering the intermediate layer (422).

Figure 17:
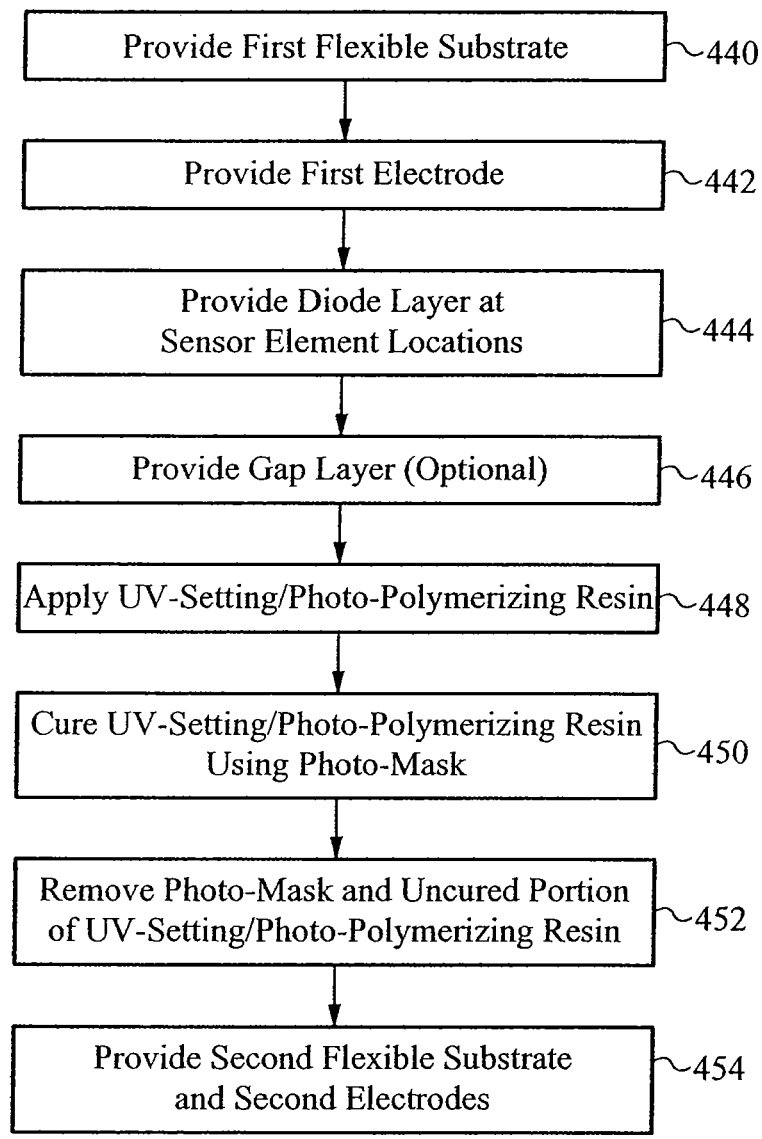
FIG. 17 is a process flow diagram schematically illustrating a method for manufacturing a biometric sensor panel having an array of sensor elements in accordance with one embodiment of the present invention.

FIG. 17 is a process flow diagram schematically illustrating a method for manufacturing a biometric sensor panel having an array of sensor elements in accordance with one embodiment of the present invention. First, a first flexible substrate is provided (440), and a plurality of first electrodes are formed on the first flexible substrate (442), in a similar manner as the previous embodiment shown FIG. 16A. Then, an intermediate layer is formed on the first flexible substrate provided with the first electrodes as follows. A diode layer is provided on the first electrode at locations where the sensor elements are to be formed (444). Providing the diode layer may include forming an N-type semiconducting polymer layer and a P-type semiconducting polymer layer on the N-type semiconductor polymer layer at the locations where the sensor elements are to be formed.

The N-type and P-type semiconducting polymer layer may be formed using photo-lithography using N-type and P-type semiconducting and photo-setting resins, respectively. For example, for N-type semiconducting polymer layer, a N-type semiconducting and photo-setting resin is applied over the first flexible substrate provided with the first electrodes, and the a N-type semiconducting and photo-setting resin is cured by irradiation of light using a photo-mask having a negative pattern for the sensor elements to be formed. That is, the N-type semiconducting and photo-setting resin is cured only at the locations where the sensor element is to be formed. Thus, after removing the photo-mask and the uncured portion of the N-type semiconducting and photo-setting resin, the N-type semiconducting polymer layer is formed on the first electrode at the location of the sensor elements. Similarly, a P-type semiconducting and photo-setting resin is then applied over the first flexible substrate provided with the first electrodes and the N-type semiconducting polymer layer, and the P-type semiconducting and photo-setting resin by irradiation of light using a photo-mask having the same negative pattern for the sensor elements to be formed, resulting in the P-type semiconducting polymer layer formed on the N-type semiconducting polymer layer at the location of the sensor elements. Alternatively, the N-type semiconducting and photo-setting resin and P-type semiconducting and photo-setting resin may be laminated first, and then cured together using the photo mask. The N-type and P-type semiconducting polymer layer may be formed using ink-jet printing or digital lithography. In place of the PN junction, a PIN junction, or a metal-semiconductor unction can be formed as the diode layer in a similar manner as described above.

Optionally, a reversible anisotropic conductive film or pressure-sensitive elastic resistive film may be formed as a gap layer on the diode layer at the locations where the sensor elements are to be formed (446).

A UV-setting or photo-polymerizing resin (photo-setting resin) is applied onto the first flexible substrate provided with the plurality of first electrodes, the diode layer, and the optional gap layer (448), and then the photo-setting resin layer is cured by irradiation of UV light (or non-UV light) using a photo-mask having a pattern of the sensor elements (450). The thickness of the cured resin layer may be greater than the thickness of the diode layer and the optional gap layer. If the optional gap layer is not formed, an air gap would be formed above the diode layer (i.e., between the diode layer and the second electrodes) in each sensor element. Then, the photo-mask and the uncured portion of the photo-setting resin are removed (452). The resulting cured resin layer forms an insulation layer surrounding the diode layer and the optional gap layer formed at each of the sensor element locations. Then, a second flexible substrate and a plurality of second electrodes arranged in a second direction on the second flexible substrate are provided such that the second electrodes face the first electrodes via the intermediate layer and the first and second electrodes cross each other at the sensor element locations (454).

This process step 454 may include (a) providing the second flexible substrate, (b) providing a plurality of second electrodes arranged in a second direction on the second flexible substrate, and (c) mounting the second flexible substrate provided with the second electrodes onto the intermediate layer such that the second electrodes face the first electrodes via hole the intermediate layer and the first and second electrodes cross each other at the sensor element locations, a gap is formed between the diode layer and the second electrodes in each of the sensor element locations. Alternatively, the process step 454 may include (a) forming the second electrodes arranged in a second direction on the intermediate layer such that the first and second electrodes cross each other at the sensor element locations, and (b) providing the second flexible substrate on the second electrodes, covering the intermediate layer.

Figure 18:
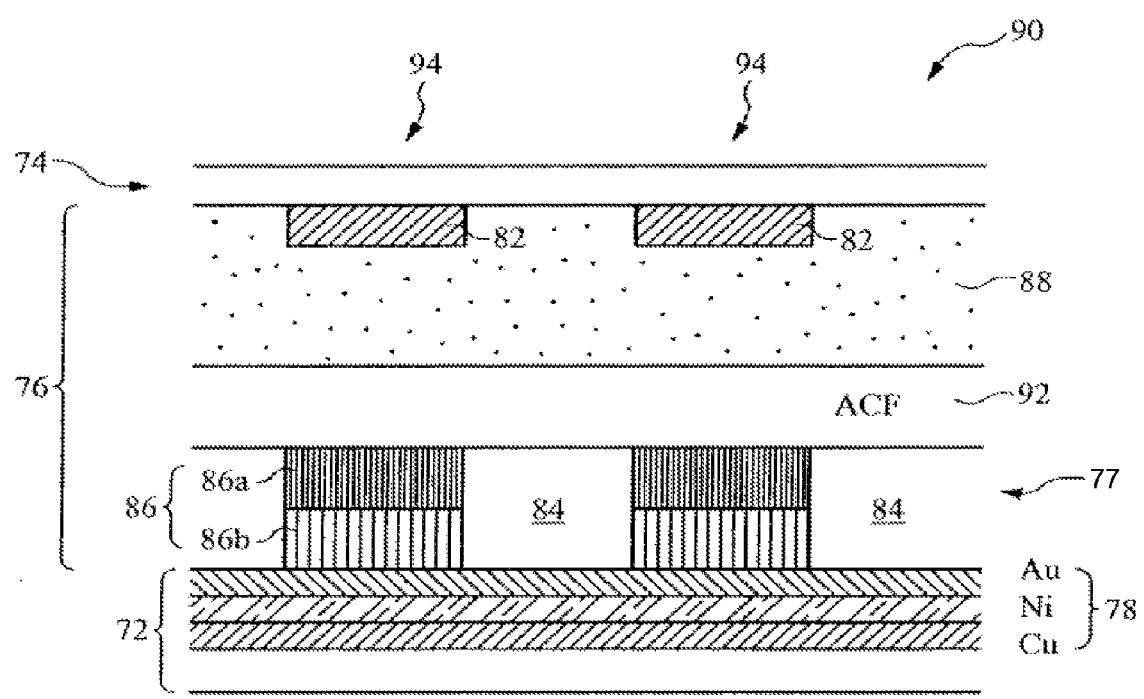
FIG. 18 is a cross-sectional diagram illustrating a sensor panel of a biometric sensor in accordance with one embodiment of the present invention.

FIG. 18 is a cross-sectional diagram illustrating a sensor panel 90 of a biometric sensor in accordance with one embodiment of the present invention. The biometric sensor panel 90 includes a first flexible substrate 72, a second flexible substrate 74, and an intermediate layer 76 provided between the first substrate 72 and the second substrate 74. The first flexible substrate 72 has a plurality of first electrodes (metal layers) 78 formed thereon and arranged in a first direction (for example, the X-direction). Similarly, the second flexible substrate 74 has a plurality of second electrodes (metal layers) 82 formed thereon and arranged in a second direction (for example, the Y-direction). The first and second flexible substrate may be made of a plastic material, such as polyimide, polyethylenenapthalate (PEN), polyester (PET), polyethelenetherketone (PEEK), polycarbonate, and the like.

The first and second electrodes 78 and 82 are also flexible. The first and second electrodes 78 and 82 may be made of metals such as Cu, Cu/Au, or Cu/Ni/Au. The first electrode 78 is illustrated as such a laminated metal layer in FIG. 18 for illustrative purpose. Indium tin oxide (ITO) may also be used for the first and/or second electrodes 78 and 82. The electrodes may be about 3-5 µm thick, about 25 µm wide, and arranged with a pitch of about 50 µm. The width (and length) of the sensor panel part may be about a half inch (or about 1.2-1.5 cm). The thickness of the sensor panel may be less than 0.4 mm. However, these materials and numbers are by way of example and are not intended to be exhaustive or limiting in any way. It should also be noted that only three each of the first and second electrodes are illustrated in the drawings for simplicity.

As shown in FIG. 18, the first electrodes 78 and the second electrodes 82 face each other via the intermediate layer 76. The intermediate layer 76 includes a diode matrix layer 77 formed by an insulation film (dry film) 84 and a flexible diode layer 86 provided in the insulation film 84 at each crossing portion of the first and second electrodes 78 and 82. For example, the insulation film 84 may be formed of a UV-setting resin or photo-polymerizing material (referred to as "photo-setting resin"). The diode layer 86 may be provided in corresponding via holes formed in the insulation film 84 at each crossing portion of the first and second electrodes 78 and 82. A pressure sensitive conductive layer 88 and an optional anisotropic conductive film (ACF) 92 are provided between the diode matrix layer 77 and the first flexible substrate 74. The pressure sensitive conductive layer 88, when depressed, conducts only in the direction of the pressure applied, and returns to a non-conductive state when the pressure is removed. For example, the pressure sensitive conductive layer 88 may use a pressure conductive rubber, such as PCR, available from JSR Microtech Inc., Saitama, Japan, or JSR Corporation, Tokyo, Japan, Pressure Sensitive Conductive Silicon Form, available from New Metals & Chemicals Ltd., Waltham Abbey Essex, United Kingdom, Pressure Activated Conductive Rubber, such as ZOFLEX®, available from Xilor Research LLC, Inc, Inastomer Pressure Conductive Rubber, available from Inaba Rubber Co. Lid, Oka, Japan, and the like. An ACF layer 92 may be provided between the pressure sensitive rubber layer 88 and the diode matrix layer 77. The ACF layer 92 only conducts in the Z-direction, i.e., the same direction as the pressure to be applied to the pressure sensitive rubber layer 88. The ACF layer 92 may also provide adhesive function between the two layers.

The diode layer 86 may be made of a polymer diode including a PN-junction, and formed by laminating a P-type polymer 86a and an N-type polymer 86b, as shown in FIG. 18. For example, conjugated polymers such as Polyaniline-Dodecyl-benzenesulfonic acid (Pani-DBSA), available as Panipol®, from Panipol Ltd., Finland, f.k.a. UNIAX Corporation, Neste Oy, Finland, which is a solution and melt processable polymer in the doped state, or Bayton P® (PEDOT-PPS), available from Bayer AG, Germany, which is a soluble polymer in the doped state, conductive polyaniline (ORMECON®), available from Ormecon AG, Germany, or polymer light emitting diodes (PLED) such as PEHPPPV, available from UNIAX Corporation, USA, Cambridge Display Technology, England, Philips, The Netherlands, COVION, Germany, and the like, can be used for the diode layer 86. In addition, the following materials may also be used for the diode layer 86: Pentacene, Copper Phthalocyanine (CuPc), diPr-phenylthio-terephthalate (PTTP), Compounds 2,3,9,10-tetramethypentacene, naphthacene (tetracene, 2,3-benzanethracene), 6,13-di substituted pentacene, 5,6,11,12-tetraphenyltetracene (rubrene), thophene oligomers, oxy-functionalized thiophene oligomers, alkoxyalkyl, tetrahydropyran (THP)-orotected 5-hydroxy, pentacene, 3,4,7,8-naphthalenetetracarboxylic diimide (NTCDI) compounds, regioregular, regiorandom poly (3-alkylthiophene), Thiophene-Phenylene, Thiophene-Thiazole Oligomeric semiconductors, 5,5'-bis(4-hexylphenyl)-2,2'-bithiophene (6PTTP6), dihexylquarterthiophene (DH4T).

Figure 19:
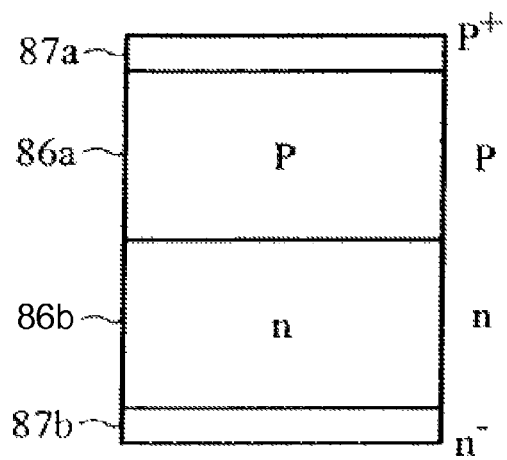
FIG. 19 is a cross-sectional diagram illustrating an example of a diode layer in accordance with one embodiment of the present invention.

For P-type polymer 86a, P-type organic semiconductor materials, such as pentacene (of good hole mobility) or conductive polymer (of good hole mobility) may be used. For N-type polymer 86b, N-type organic semiconductors such as perfluorinated pentacene with electron-withdrawing elements attached at molecular terminals, and fullerene derivative ([6,6]-phenyl C61-butyric acid methyl ester, PCBM) may be used. Furthermore, fullerene (C60) of soccer ball-like construction is known to have highest electron mobility despite its simple structure, and a synthesized fullerene derivative (C60-fused pyrrolidine-meta-C12 phenyl: C60MC 12) with 12-carbon alkyl chain incorporated to fullerene (C60), and the like, may be used. The diode layer 86 may also be a light emitting diode. If a light emitting diode is used for the diode layer 86, the sensor panel part may be part of, or used as, a display, by providing a driving circuit for the display function and using transparent materials above the intermediate layer 36. The diode layer 86 may have a $P+$ layer 87a on the P-type polymer layer 86a, and an N-layer 87b on the N-type polymer layer 86b, as shown in FIG. 19.

Alternatively, the diode layer 86 may include a PIN junction, or may be a Schottky diode including a metal-semiconductor junction. P-type and/or N-type semiconducting polymers may be used for the PIN or Schottky diode in a similar manner as those described above. An insulating polymer layer may be formed between the P-type and N-type semiconducting polymer layer in order to form a PIN junction. Using Schottky diode requires only one polymer layer, and thus the structure of the sensor element can be very simple and made using a short process. The Schottky diode may include a junction between metal and a N-type polymer, P-type polymer, and/or I-type polymer. The metal may also be Indium Thin Oxide (ITO). Schottky diode also has other advantages such as fast switching speed, low forward voltage drop, and hot carrier. For example, if logic devices such as CMOS are used with the supply voltage Vcc of 3.3 volt, the threshold voltage Vth would be 1.6 volt. If driver logic is operated at 3.3 volt, the output voltage Vf of a PN polymer junction may be 2 volt, since regardless of the applied voltage, the output voltage Vf is always higher than Vth. However, in case of Schottky diode, the output voltage Vf may be 0.3-0.5 volt, which gives sufficient voltage for sensor elements.

Similarly to the above-described embodiments, at each crossing of the first electrode 78 and the second electrode 82, a passive sensor element 94 is formed. That is, the corresponding part of the first and second electrodes 78 and 82, the diode layer 86, pressure sensitive conductive layer 88, and the optional ACF 92 form a sensor element 94. The pressure sensitive conductive layer 88 prevents the second electrode 82 from electrically connected to the diode layer 86, or otherwise provides a sufficiently high resistance such that the second electrode 82 is electrically disconnected from the diode layer 86, when there is no deformation of the second flexible substrate 74 (i.e., no finger is placed on the sensor panel 90). Since the pressure sensitive conductive layer 88 provides a pressure sensitive switching function, the ACF 92 is not necessarily reversible in this embodiment. The ACF 92 may be an anisotropic conductive adhesive. Alternatively, the gap 52 may be formed of a reversible anisotropic conductive film (ACF), which conducts, only when pressed, in the direction of the pressure. The intermediate layer 76 provides electrical connection between the second electrode 82 and the diode layer 86 only when the corresponding sensor element 94 is depressed by a biometric pattern.

The pressure sensitive conductive layer 88 (coupled with the diode layer 86 and the second electrode 82) operates as a switching element which conducts (ON state) in accordance with the biometric pattern. The diode layer 86 provides an ON current in a specific direction (from the second electrode 82 to the first electrode 78 in this example), which prevents unwanted current flows and cross talks between sensor elements 94. The biometric sensor panel 90 may be manufactured in a similar manner as other biometric sensor panels described above.

Figure 20:
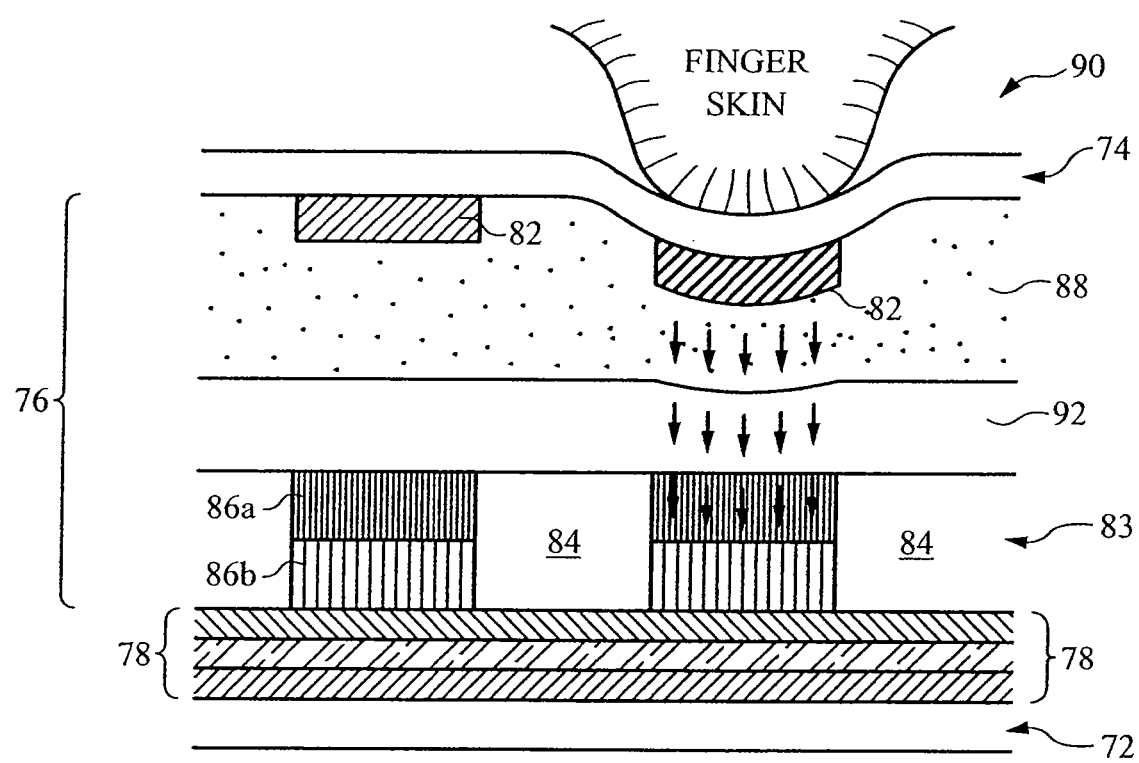
FIG. 20 is a cross-sectional diagram schematically illustrating a biometric sensor panel being touched by a finger, in accordance with one embodiment of the present invention.

FIG. 20 is a cross-sectional diagram schematically illustrating a biometric sensor panel being touched by a finger, in accordance with one embodiment of the present invention. As shown in FIG. 20, the second substrate 74 is deformed in accordance with the fingerprint pattern. A ridge of the fingerprint pattern depresses the second substrate 74 towards the first substrate 72 such that the corresponding second electrode 78 moves downward and depresses the pressure sensitive conductive layer 88 into its conductive state. Thus, the sensor elements 94 which are depressed by the ridge of the fingerprint pattern provide an electrical connection between the first and second electrodes 72 and 74 via the pressure sensitive conductive layer 88, the ACF 92, and the diode layer 86 (i.e., ON state), while other sensor elements 94 which are not depressed by the fingerprint pattern are in a OFF state. Such a pressure sensitive conductive layer 88 may be an elastic material layer containing conductive particles or metallizations formed of one or more materials selected from the group consisting of: Cr/Ni, Cr/Ni/Au, Ti/Ni, Ti/Ni/Au, Cr/Cu, Cr/Cu/Au, Ti/Cu, Ti/Cu/Au, Cr/Al, Cr/Al/Au, Ti/Al, Ti/Al/Au, Cr/Ag, Cr/Ag/Au, Ti/Ag, Ti/Ag/Au, Al, Au, Ni, and TiN.

Figure 21A:
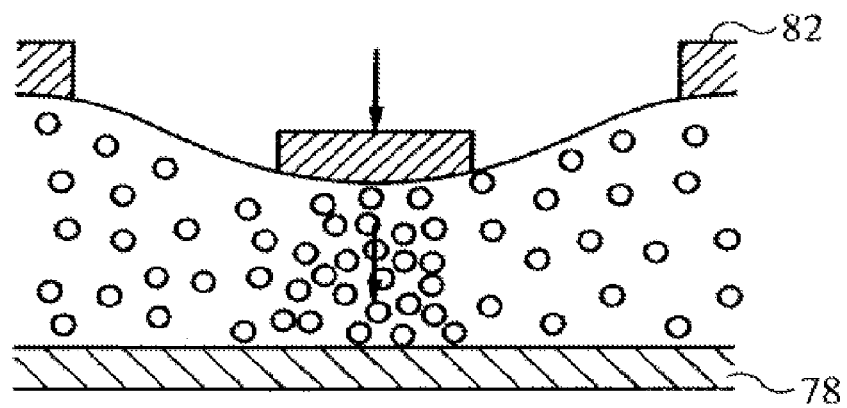
FIGS. 21A and 21B are, respectively, cross-sectional diagrams illustrating examples of biometric sensor panel formed with various densities of pressure sensitive conductive layers in accordance with embodiments of the present invention.
Figure 21B:
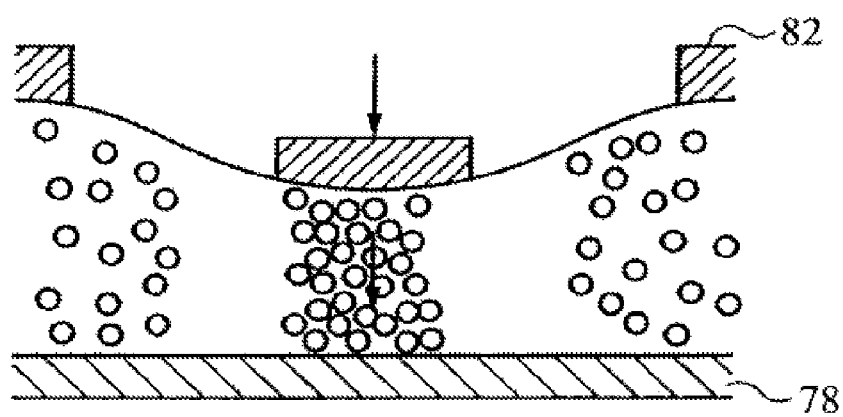

FIGS. 21A and 21B are, respectively, cross-sectional diagrams illustrating examples of biometric sensor panel formed with various densities of pressure sensitive conductive layers in accordance with embodiments of the present invention. The pressure sensitive conductive layer 88 may be formed of a insulating resin or rubber dispersed with conducive particles, as described above. When the pressure sensitive conductive layer 88 is depressed, the conductive particles come into contact with each other and realize a conductive state at the depressed portion. Such dispersion of the conductive particles may be substantially uniform, as shown in FIG. 21A. Alternatively, the conductive particles may be selectively provided at the crossing portion of the first and second electrodes 78 and 82, as shown in FIG. 21B.

In addition, the biometric sensor panel 90 may further include a flexible protective layer formed on the second substrate 74, similarly to the flexible protective layer 58 (in FIGS. 7-8), a plurality of tactile location bumps formed on the protective layer, similarly to the plurality of tactile location bumps 62 (in FIGS. 8 and 9), and/or a back layer having a plurality of bumps (lower support bumps), similarly to the back layer 54 having the plurality of bumps (lower support bumps) 56 (in FIGS. 7 and 9) as described above.

Figure 22A:
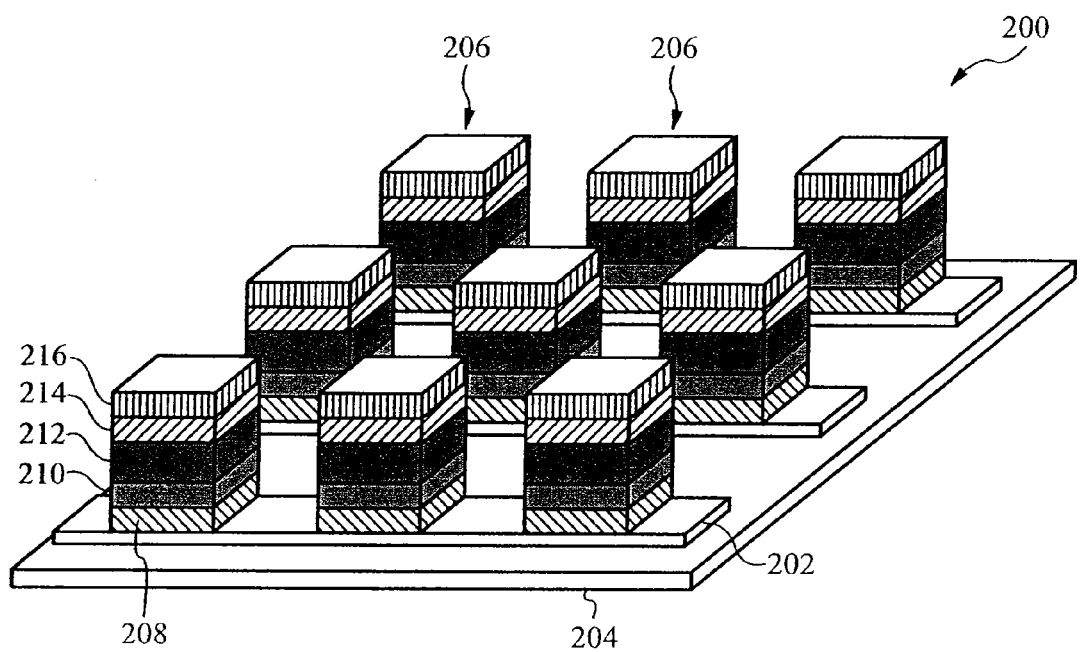
FIG. 22A is a perspective diagram illustrating a diode array for a sensor panel in accordance with one embodiment of the present invention.
Figure 22B:
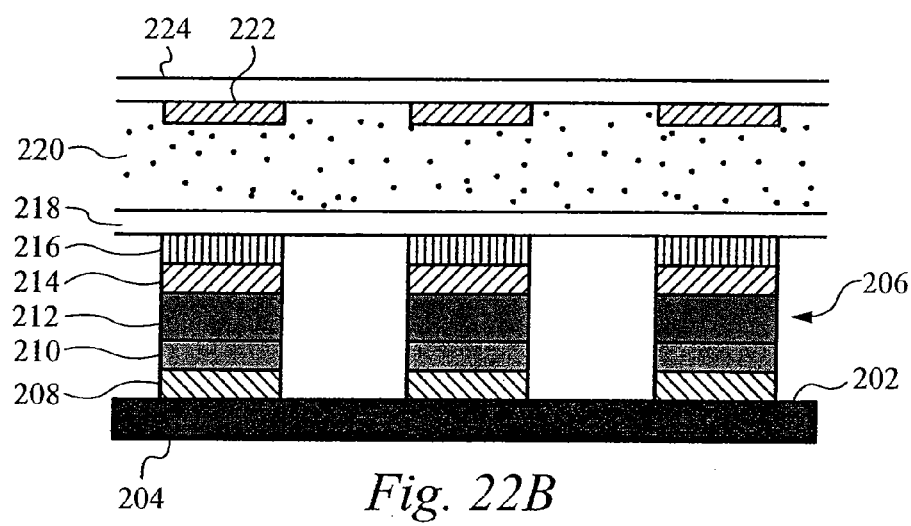
FIG. 22B is a cross-sectional diagram taken along line 22B-22B of FIG. 22A illustrating the diode array structure of FIG. 22A.

FIG. 22A is a perspective diagram illustrating a diode array for a sensor panel in accordance with one embodiment of the present invention. FIG. 22B is a cross-sectional diagram taken along line 22B-22B of FIG. 22A illustrating the diode array structure of FIG. 22A. In the diode array 200, a plurality of diode elements 206, for example, p-n($p^+$,p,n,n) junctions, are arranged in a matrix. In this example, a plurality of first electrodes (metal layers) 202 are formed on a flexible substrate 204, and diode elements 206 are provided on the first electrodes 202. Each diode element 206 includes, from the first electrode side, n, n, p, and $p^+$ layers 208-214. The diode element 206 also includes a metal layer 216 providing ohmic contact with upper layers (not shown in FIG. 22A). As shown in FIG. 22B, an ACF layer 218, a pressure sensitive conductive layer 220, a plurality of second electrodes 222, and an upper substrate 224 are formed on and above the diode array 200. Materials of these layers may one of those described in the previous embodiments.

The flexible substrate 204 is, for example, made of polyimide, and have sufficient bending resistance. In each diode element 206, the first electrode 202 may be made of Au, ITO, Cu, and/or Ni, and acts as a cathode, while the metal layer (ohmic contact) 216 acts as an anode. In accordance with one embodiment of the present invention, each of the diode elements 206 has an area (corresponding to device width W) of about 25 µm×25 µm, a thickness (corresponding to device length L) smaller than about 30 µm. The diode elements 206 may be arranged in a matrix with pitch 50 µm, or in other arrangement, for example, an arrays with staggered row or columns. The diode elements 206 may also be made of other type of diode, for example, a vertical Schottky diode. The space between the diode elements 206 and between the ACF 218 and the first electrodes 202 (the flexible substrate 204 may be filled with an insulator providing electric insulation between adjacent diode elements 206 and between the ACF 218 and the first electrodes 202.

The diode element 206 may have the following electrical characteristics, in accordance with one embodiment of the present invention:

Forward drop <1.0 V at an operating current, preferably <0.5 V at 0.1 mA

Switching frequency of 5 MHz

Reverse breakdown voltage of about 10 V

If/Ir (Forward current/Reverse current) >1000

Figure 23:
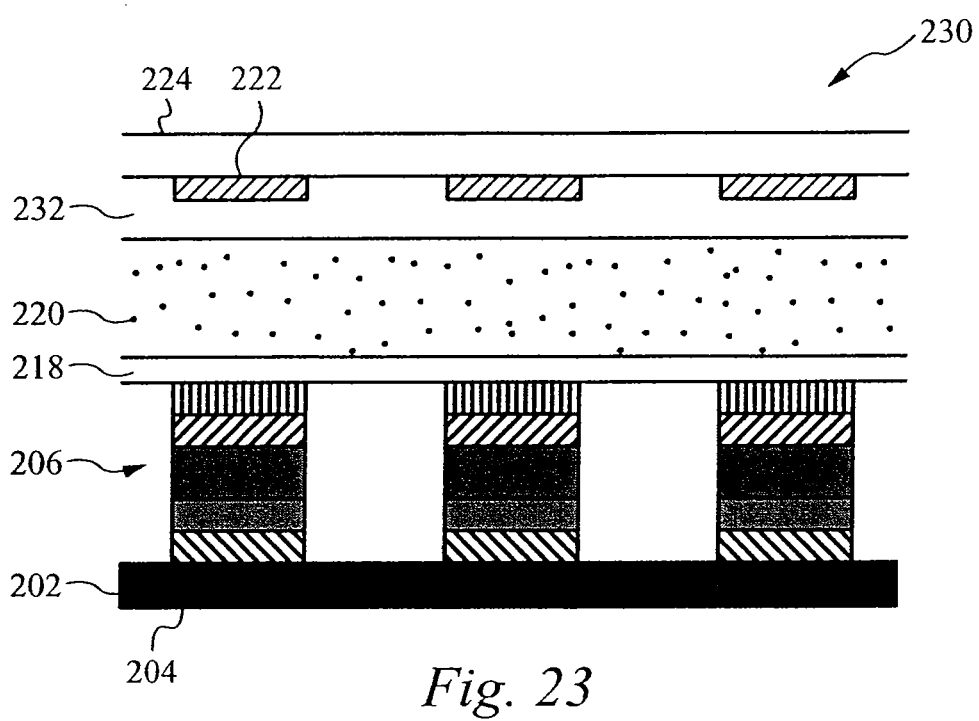
FIG. 23 is a cross-sectional diagram illustrating a sensor panel in accordance with one embodiment of the present invention.

FIG. 23 is a cross-sectional diagram illustrating a sensor panel in accordance with one embodiment of the present invention. As shown in FIG. 23, a second ACF layer 232 is provided on the pressure sensitive conductive layer 220. In FIG. 23, the like elements bear the like numbers as those in FIG. 22B.

Figure 24:
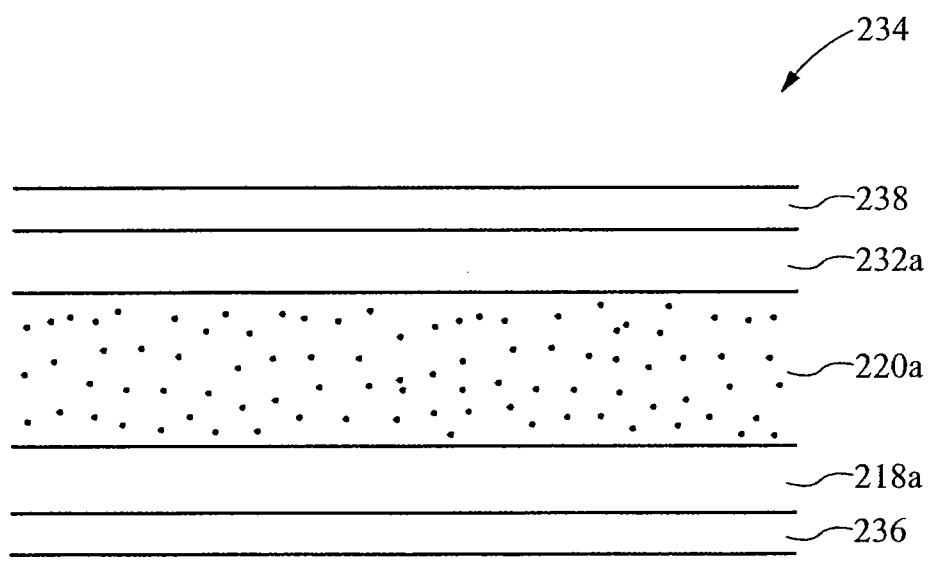
FIG. 24 is a cross-sectional diagram illustrating a pressure sensitive conductive flexible sheet in accordance with one embodiment of the present invention.

FIG. 24 is a cross-sectional diagram illustrating a pressure sensitive conductive flexible sheet in accordance with one embodiment of the present invention. As shown in FIG. 24, the pressure sensitive conductive flexible sheet 234 includes a pressure sensitive conductive layer 220a, a first ACF layer 218a and a second ACF layer 232a formed on the respective sides of the pressure sensitive conductive layer 220a, a first protective film 236, formed on the first ACF layer 218a, and a second protective film 238 formed on the second ACF layer 232a.

For example, the pressure sensitive conductive layer 220a may have a thickness between 20-100μ, preferably about 50μ, the first and second ACF layer 218a and 232a may have a thickness between 10-50μ, preferably about 20μ, and first and second protective films 236 and 238 may have a thickness between 10-500μ. The first and second ACF layers 218a and 232a may include a respective thermosetting resin having a different curing temperature. For example, a curing temperature $T_1$ of the first ACF layer 218a is higher than a curing temperature $T_2$ of the second ACF layer 232a. Alternatively, the first ACF layer 218a may include a thermosetting resin, and the second ACF layer 232a may include a photo or UV-setting resin. The first and second protective layers protect the first and second ACF layer 218a and 232a (and the pressure sensitive conductive layer 220a therebetween) during handling, and are easily peeled off from the first and second ACF layer 218a and 232a, respectively. Since the curing characteristics of the first and second ACF layer 218a and 232a are different, as mentioned above, the first and second protective films may have a different color, or other markings on their surface, to indicate which side of the pressure sensitive conductive rubber sheet 234.

When the sensor panel 230 is manufactured, the pressure sensitive rubber sheet 234 may be sued as follows. For example, suppose that the first substrate 204 having the first electrodes 202 and the diode elements 206, and the second substrate 224 having the second electrodes 222 are prepared separately, using processes described above. The second protective film 238 is peeled off and the second substrate 224 (provided with the second electrodes 222) is attached to the pressure sensitive conductive layer 232a via the second ACF layer 238. By a photo/UV-setting or thermosetting process, the second ACF layer 238 is adhered to the second substrate 224. Since the first ACF layer 218a is thermosetting (at a higher temperature if the second ACF layer is also thermosetting), the first ACF layer 218a is not affected by the exposure to the light or lower temperature during the assembling process. Then, the first protective film 236 is removed, and the first substrate 204 (provided with the electrodes 202 and the diode array 206) is adhered to the pressure sensitive conductive layer 222a via the first ACF layer 236 by thermosetting the first ACF layer 218a in a similar manner.

It should be noted that the diode elements 206 (diode array) may be formed and patterned using one or more photo/UV-setting (or photo-hardening) semiconducting polymers. Alternatively, the diode elements 206 may be formed and patterned using one or more photo/UV-decomposing semi-conducting polymers. Thus, it is preferable not to use a photo/UV setting process onto the first substrate on which the diode array has been formed.

Figure 25A:
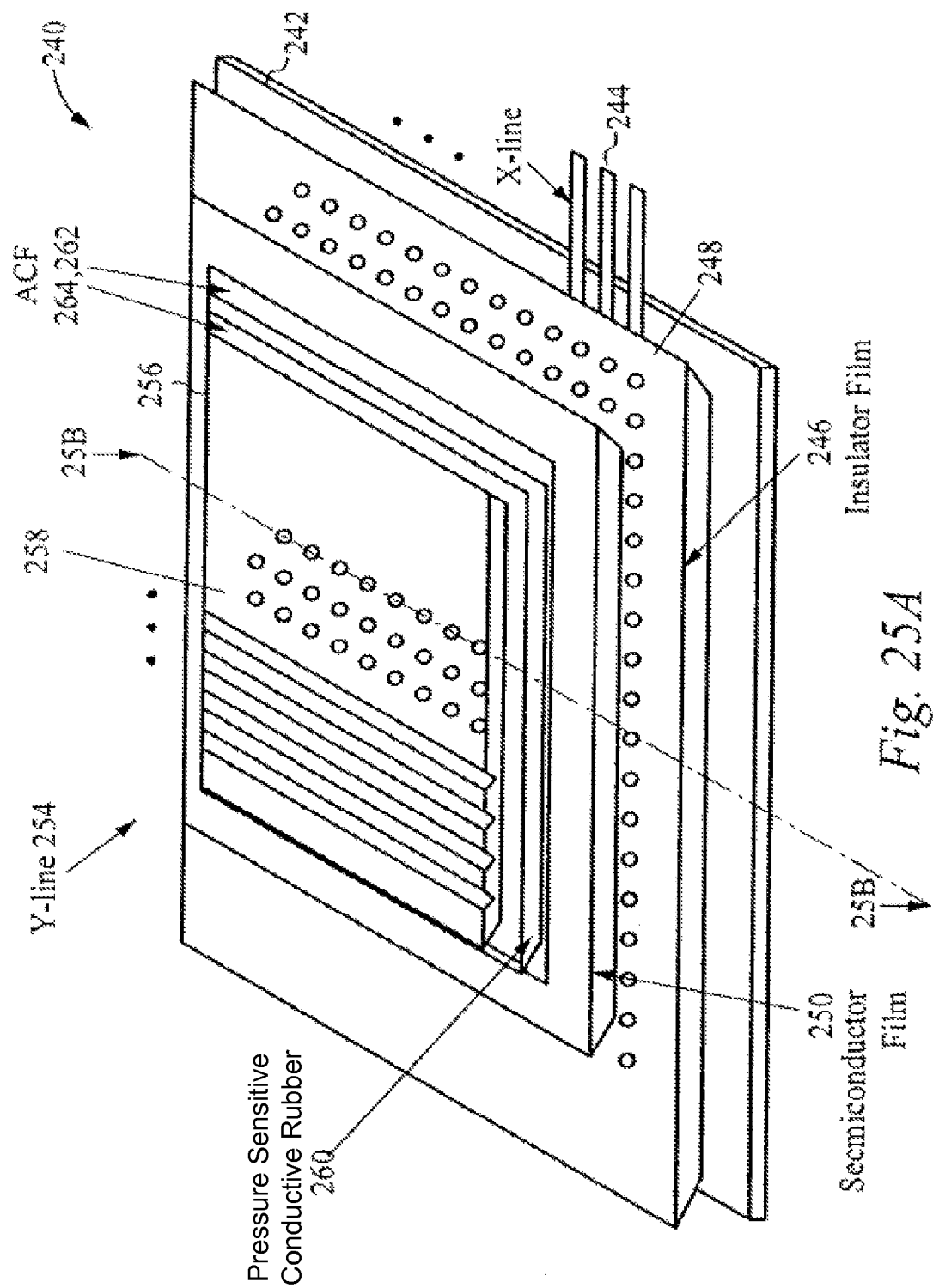
FIG. 25A is a perspective diagram illustrating a biometric sensor panel in accordance with one embodiment of the present invention.
Figure 25B:
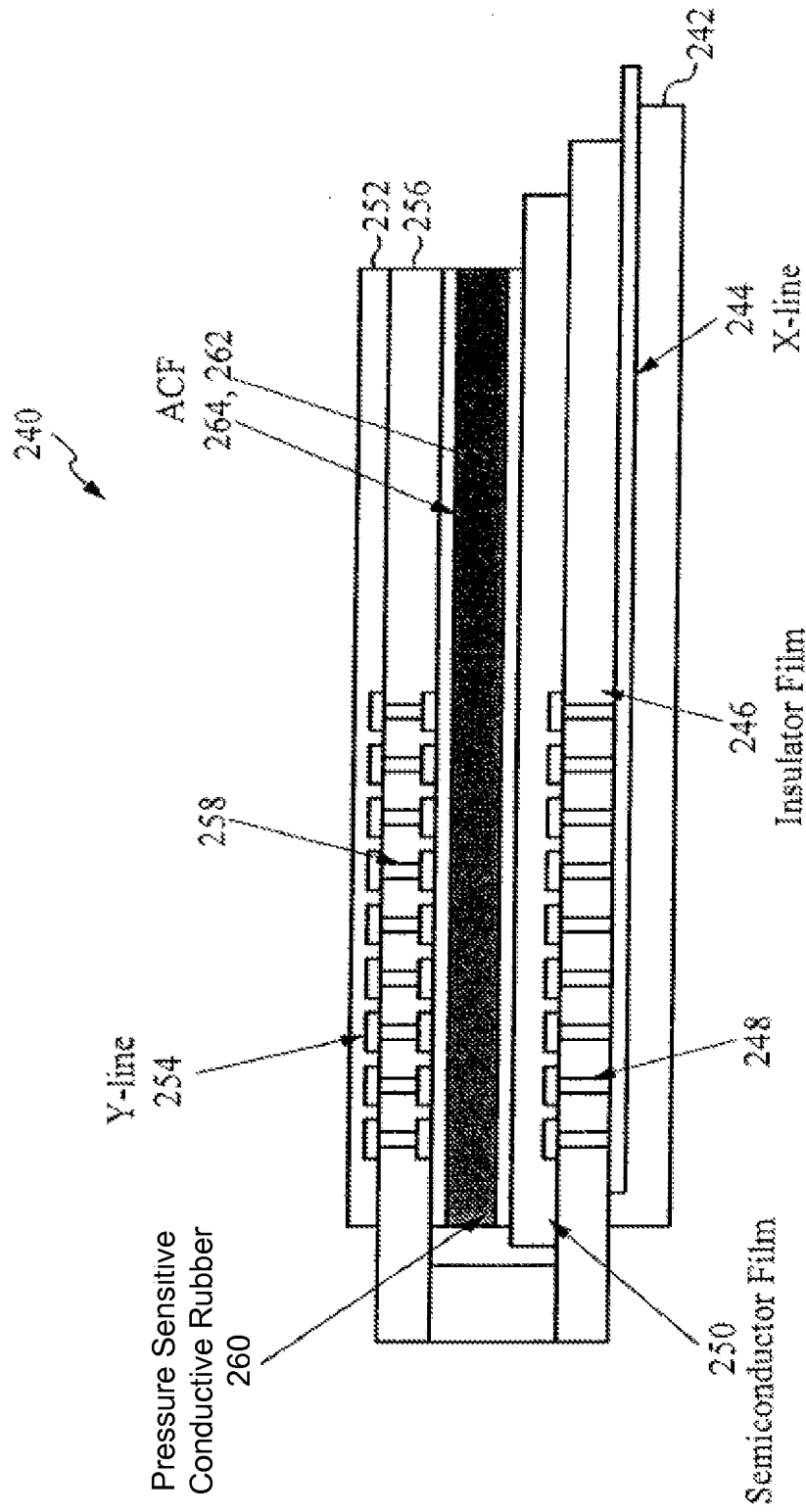
FIG. 25B is a cross-sectional diagrams taken along line 25B-25B of FIG. 25A illustrating the biometric sensor panel of FIG. 25A.

FIG. 25A is a perspective diagram illustrating a biometric sensor panel 240 in accordance with one embodiment of the present invention. FIG. 25B is a cross-sectional diagrams taken along line 25B-25B of FIG. 25A illustrating the biometric sensor panel of FIG. 25A. As shown in the figures, the biometric sensor panel 240 includes a first flexible substrate 242, a plurality of first electrodes 244 formed on the first flexible substrate 242, a first insulation layer 246 formed on the first electrodes 244 over the first flexible substrate 242, a plurality of first contact pads 248 formed on the first insulation layer 246, a semiconductor layer 250 formed on the first contact pads 248 over the first insulation layer 246. The first electrodes 244 are arranged in a first direction (for example, X-direction), and the first contact pads 248 are aligned with the first electrodes 242 and connected to corresponding one of the first electrodes 242 through via holes formed in the first insulation layer 246, The biometric sensor panel 242 further includes a second flexible substrate 252 (not shown in FIG. 25A), a plurality of second electrodes 254 formed on the second flexible substrate 252, a second insulation layer 256 formed on the second electrodes 254 over the second flexible substrate 252, a plurality of second contact pads 258 formed on the second insulation layer 256, and a pressure sensitive conductive layer 260. The second electrodes 254 are arranged in a second direction (for example, Y-direction) crossing the first direction, and the second contact pads 258 are aligned with the second electrodes 254 and connected to corresponding one of the second electrodes 254 through via holes formed in the second insulation layer 256.

As shown in FIG. 25B, the first and second flexible substrates 242 and 252 face each other such that each of the first contact pads 248 aligns with corresponding one of the second contact pads 258 via the semiconductor layer 250 and the pressure sensitive conductive layer 260 sandwiched therebetween. In accordance with one embodiment of the present invention, the biometric sensor panel 240 may further includes a first anisotropic conductive film (ACF) 262 formed on the pressure sensitive conductive layer 260 connecting the pressure sensitive conductive layer 260 and the semiconductor layer 250, and a second ACF 264 formed on the pressure sensitive conductive layer 260 connecting the pressure sensitive conductive layer 260 and the second contact pads 258.

The semiconductor layer (polymer semiconductor film) 250 functions as a single intrinsic semiconductor in combination with the contact pads 248 (conductor), forming a Schottky barrier diode. By controlling the thickness and the space between adjacent contact pads 248, such an intrinsic semiconductor has sufficient resistivity in the horizontal direction (or all directions other than that of the current flow) and thus the cross talk between adjacent contact pads 248 would be negligible. In this embodiment, patterning of semiconductor to separate diode elements is unnecessary, and thus the manufacturing process can be simplified.

Figure 26:
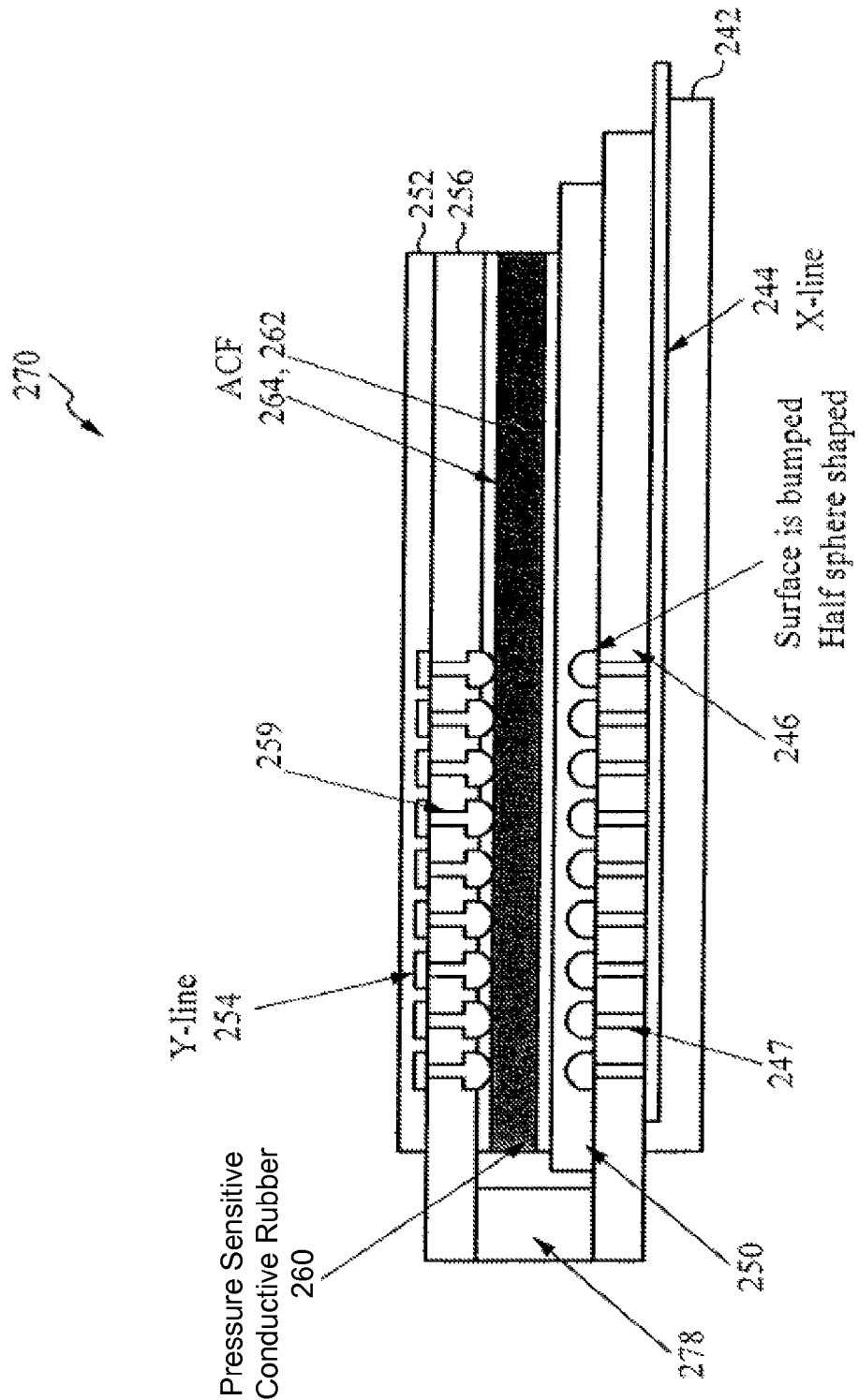
FIG. 26 is a diagram similar to that of FIG. 25B but illustrating a modification thereof in accordance with one embodiment of the present invention.

FIG. 26 is a diagram similar to that of FIG. 25B but illustrating a modification thereof in accordance with one embodiment of the present invention. The difference between the biometric sensor panes 270 and 240 is in that each of the first second contact pads 249 and 259 in the biometric sensor panel 270 is formed in a bump shape protruding toward the pressure sensitive conductive layer 260. For example, each of the pads may have a half sphere shape. By providing the contact pads with a bump/protruding shape, more localized pressure can be applied to the pressure sensitive conductive layer 260, reducing crosstalk between the adjacent diode elements.

In manufacturing the biometric sensor panel 270 (or 240), the first substrate 242 and the second substrate 252 may be separately formed, where the first substrate 242 has the first electrodes 244, the first insulation layer 246, the first contact pads 249, and the semiconductor layer 250 thereon, and the second substrate 252 has the second electrodes 244, the second insulation layer 256, and the second contact pads 259 thereon. Then, the pressure sensitive conductive layer 260 on which the ACFs 262 and 264 are provided, are inserted between thus prepared first and second substrates. The first and second substrates 242 and 256 may be pre-connected by a connecting member 278 prior to inserting the pressure sensitive conductive layer 260 (provided with ACFs 262 and 264), or forming the semiconductor layer 250 for the X-Y alignment of the first and second electrodes 244 and 252.

Figure 27:
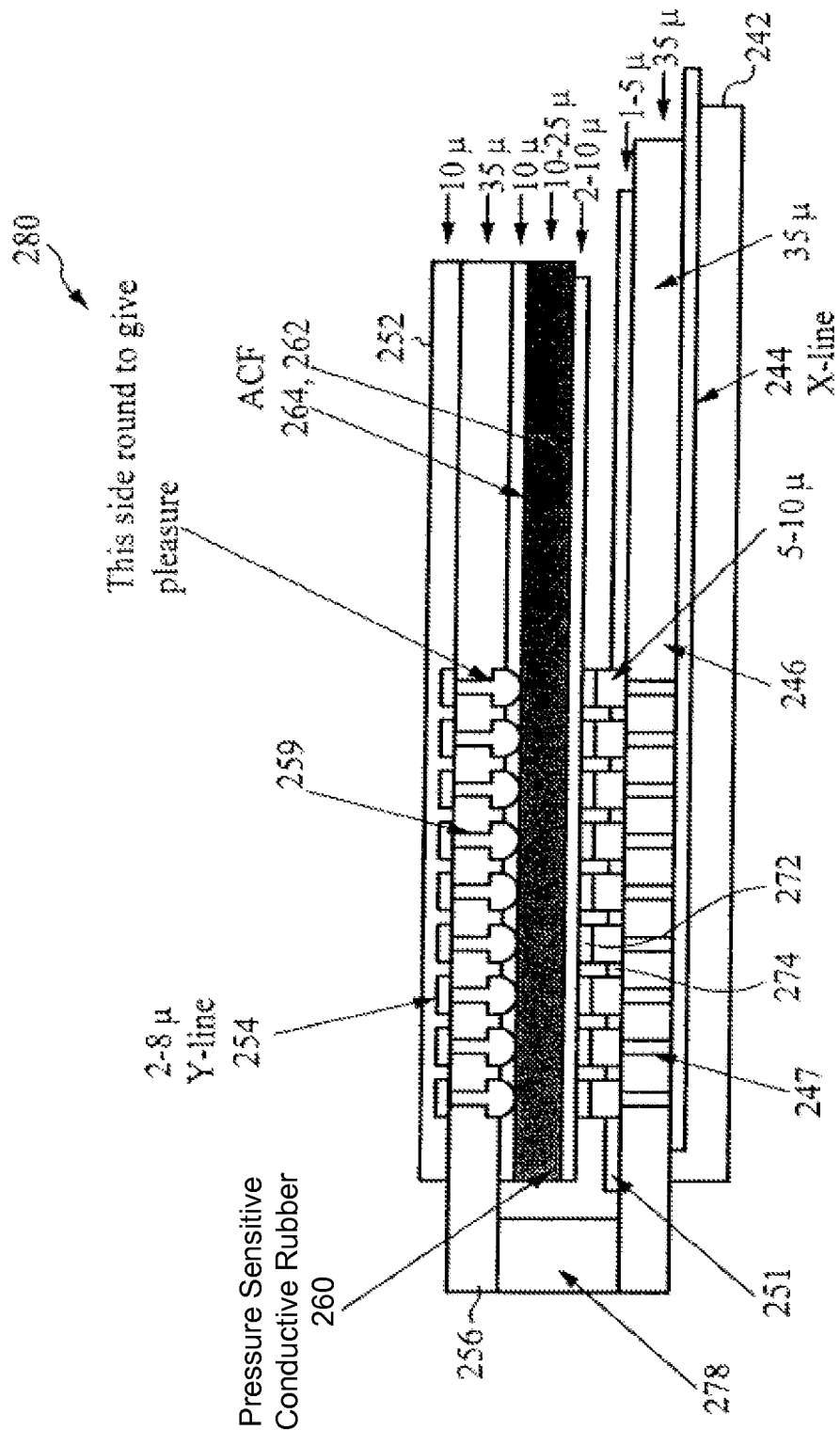
FIG. 27 is a diagram similar to that of FIG. 25B but illustrating a modification thereof in accordance with one embodiment of the present invention.

FIG. 27 is a diagram similar to that of FIG. 25B but illustrating a modification thereof in accordance with one embodiment of the present invention. In the biometric sensor panel 280, each of the second contact pads 259 is provided with a bump and has a protruding shape, similarly to the biometric sensor panel 270 described above. The first contact pads 247 are similar to the first contact pads 248 in the biometric sensor panel 240 (see FIG. 25B), but have a greater thickness such that the semiconductor layer 251 formed thereon does not cover the steps. That is, the thickness of the first contact pads 247 is greater than that of the semiconductor layer 251, and thus each portion 272 of the semiconductor layer 251 formed on the first contact pads 247 is isolated from the remaining portion 274 of the semiconductor layer 251 formed directly on the first insulation layer 246. As shown in FIG. 27, the remaining portion 274 of the semiconductor layer 251 formed directly on the first insulation layer 247 is not in contact with the first ACF 262. Since portions 272 of the semiconductor layer 251 formed on the first contact pads 247 are isolated each other by the gap between the adjacent first contact pads 247, this structure also reduces the crosstalk between the adjacent diode elements. FIG. 27 also shows example of the thickness of each layer. However, the numbers are all illustrative and not limiting in any way.

Figure 28A:
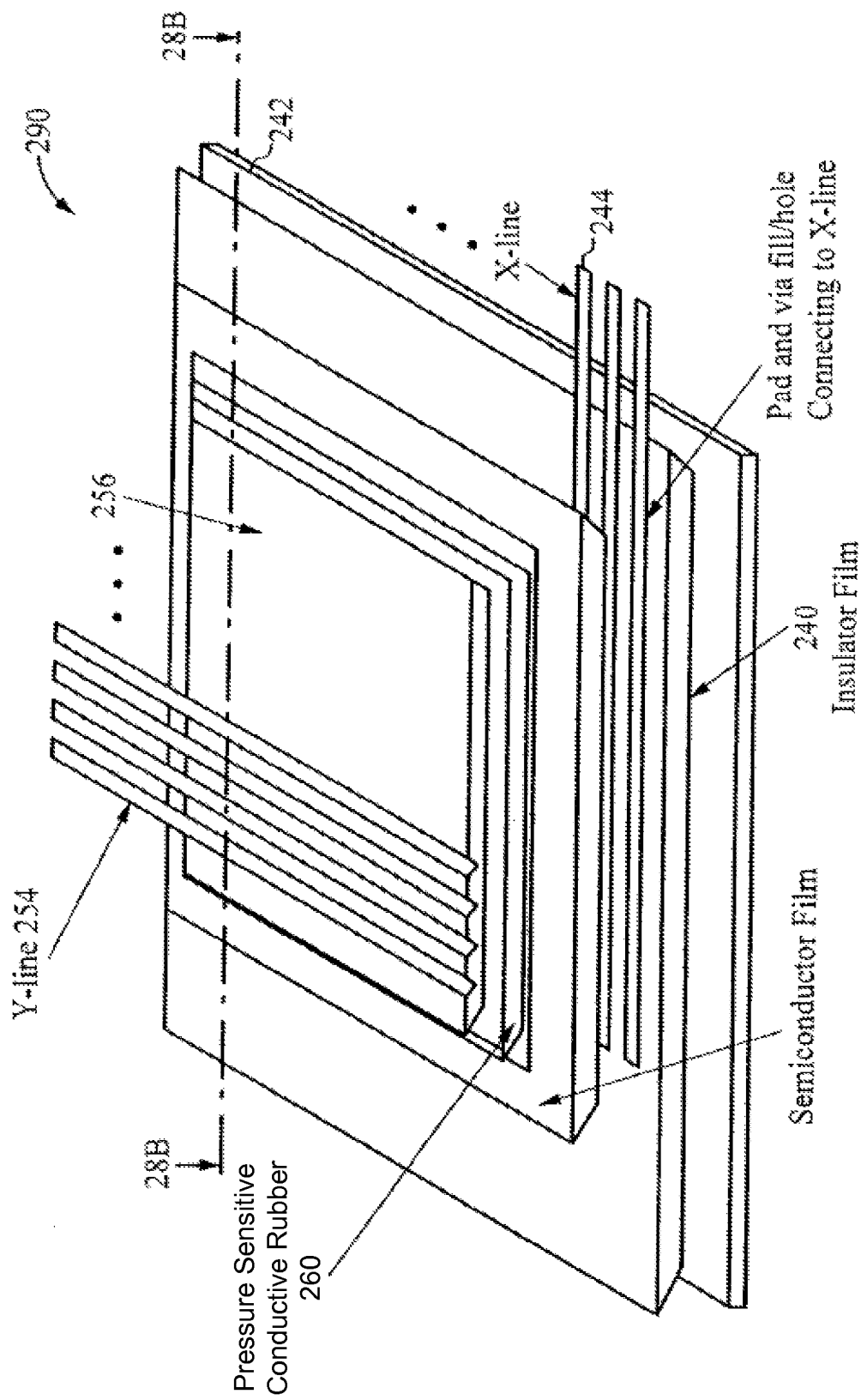
FIG. 28A is a perspective diagram schematically illustrating a biometric sensor panel in accordance with one embodiment of the present invention.
Figure 28B:
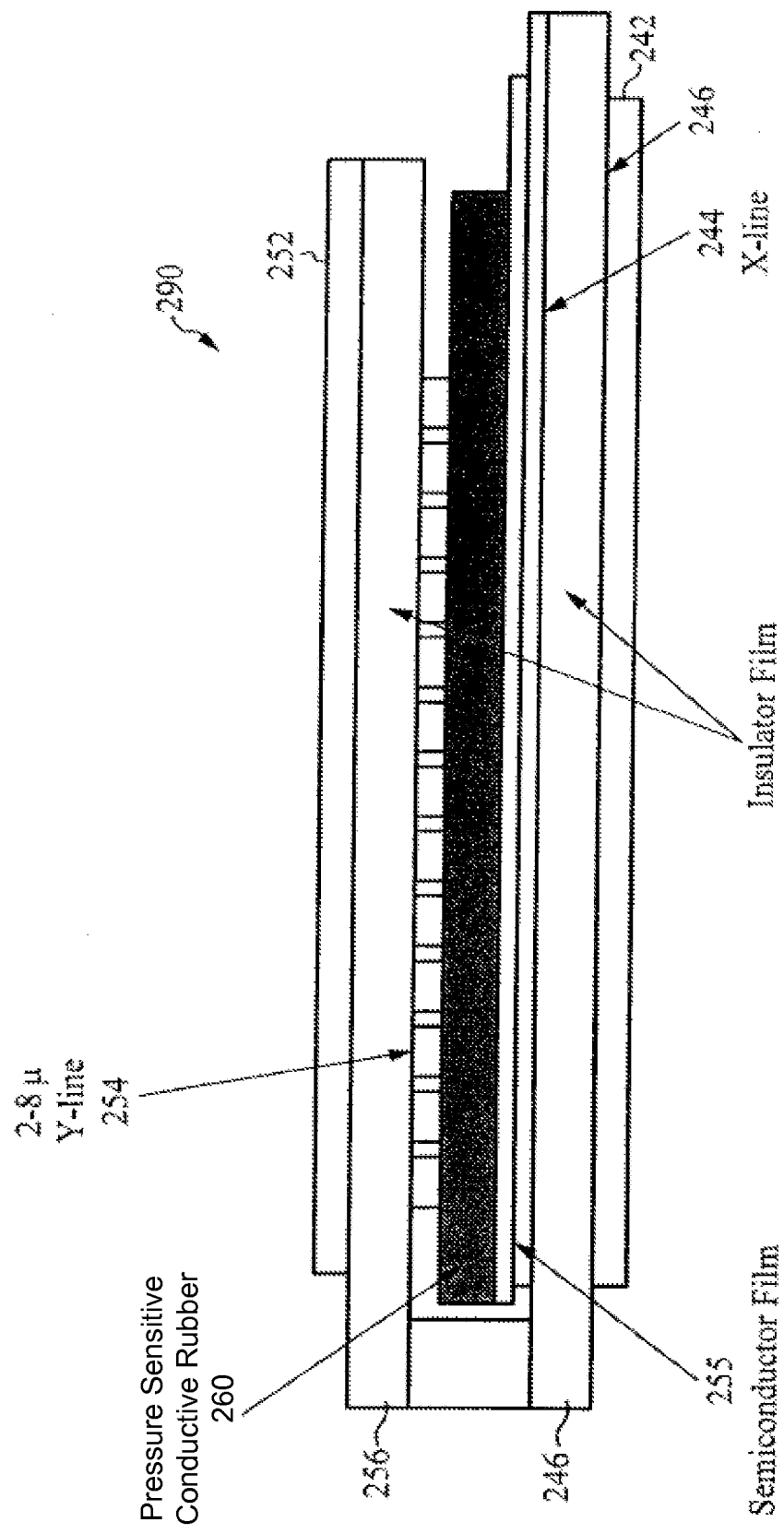
FIG. 28B is a cross-sectional diagram taken along line 28B-28B of FIG. 28A.

FIG. 28A is a perspective diagram schematically illustrating a biometric sensor panel in accordance with one embodiment of the present invention. FIG. 28B is a cross-sectional diagram taken along line 28B-28B of FIG. 28A. Like components in the biometric sensor panel 290 are referenced by the like numerals in the biometric sensor panel 240 described above. As shown in FIGS. 28A and 28B, the biometric sensor panel 290 includes a first flexible substrate 242, a plurality of first electrodes 244 formed on the first flexible substrate 242, a semiconductor layer 255 formed on the first electrodes 244, a second flexible substrate 252 (not shown in FIG. 28A), a plurality of second electrodes 254 formed on the second flexible substrate 252, and a pressure sensitive conductive layer 260 formed on the second electrodes 254. As shown in FIG. 28B, the biometric sensor panel further includes a first insulation layer 246 formed between the first electrodes 244 and the first flexible substrate 242, and a second insulation layer 256 formed between the second electrodes 254 and the second flexible substrate 252.

For example, the first and second electrodes 242 and 252 may have a thickness of about 10 µm, the first and second electrodes 244 and 254 may have a thickness of about 2-8 µm, the first and second insulation layers 246 and 256 may have a thickness of about 35 µm, the semiconductor film 255 may have a thickness of about 1-5 µm, and the pressure sensitive conductive layer 260 may have a thickness of about 10-25 µm. The first electrodes 244 are arranged in a first direction (for example, X-direction), and the second electrodes 254 are arranged in a second direction (for example, Y-direction) crossing the first direction. The first and second flexible substrates 242 and 252 face each other such that the semiconductor layer 244 is in contact with the pressure sensitive conductive layer 260. The first and second electrodes 244 and 254 may have a laminated structure, including a Cu layer, Ni layer, and Au layer in this order from the bottom. The top Au layer is a contact layer contacting the semiconductor layer 255 (for the first electrode 244) or the pressure sensitive conductive layer 260 (for the second electrode 254).

The biometric sensor panel 290 has a simpler structure compared with that of the biometric sensor panels 240, 270, and 280, but it eliminates AFCs, contact pads, and via holes. The semiconductor layer 255 may be formed by spraying, spin coating, or laminations. The pressure sensitive conductive layer (rubber) 260 may be form-based, silicon-based, or the like, and may be formed by spin coating or laminations. For example, elastic resin in which conductive particles such as gold, carbon or silver particles having a diameter less than one micron are dispersed, may be screen printed, spin coated, film-laminated, or doctor-bladed. In addition, spaces between the electrodes (lines) may be filled with an insulator, such as a photo-resist or polyimide. In this configuration, strict alignment among the layers, including the first and second electrode alignment, is not required. The surface of the second electrode 254 may be curved outwardly to have a convex face so as to apply more localized and stronger pressure onto the pressure sensitive conductive layer. For example, the second electrodes has a barrel roof shape protruding toward the pressure sensitive conductive layer.

Figure 29:
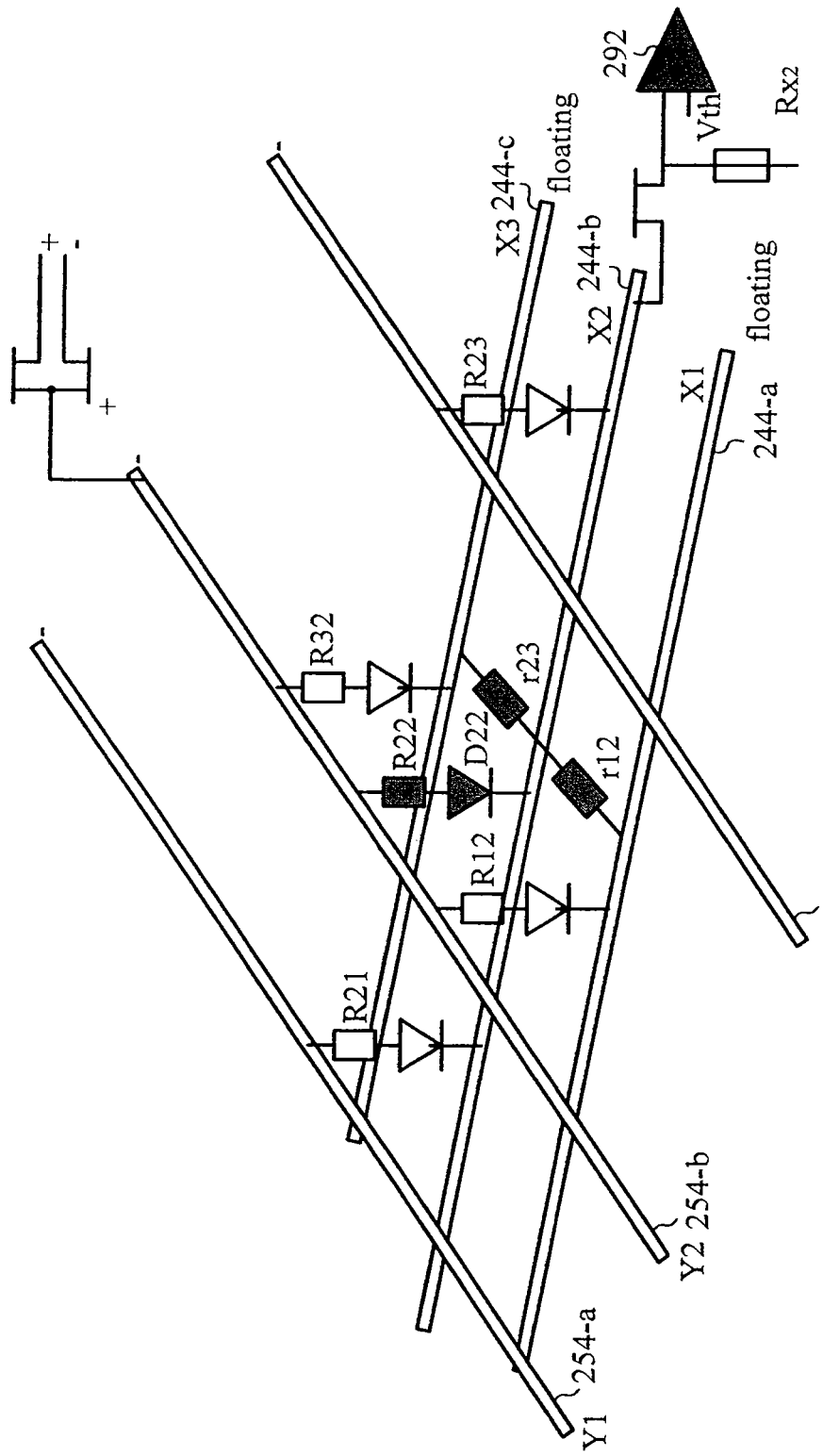
FIG. 29 is a diagram schematically illustrating a crosstalk analysis for a biometric sensor panel in accordance with one embodiment of the present invention.

FIG. 29 is a diagram schematically illustrating a crosstalk analysis for a biometric sensor panel in accordance with one embodiment of the present invention. FIG. 29 shows three first electrodes 244-a (X1), 244-b (X2), and 244-c (X3), and three second electrodes 254-a (Y1), 254-b (Y2), and 254-c (Y3). A diode element formed at the crossing of the first electrode Xn and the second electrode Ym is referred to as Dnm, and the corresponding resistance of the pressure conductive layer 260 at the first and second electrodes Xn and Ym is referred to as Rmn. When reading out the captured pattern from the diode elements array, the second electrodes 254 are sequentially selected, and the selected electrode (Y-line) is applied with a positive voltage. Unselected second electrodes 254 may be at the ground level, or applied with a negative voltage. For each selected second electrode (Y-line), the first electrodes 244 are sequentially selected ("sensed") and signals therefrom are coupled to an operational amplifier 292 or to a read circuit (not shown). Unselected first electrodes 244 may be supplied with a positive voltage or otherwise in a floating state.

In this example, the diode element D22 formed between the first electrode X2 and the second electrode Y2 is pressured by the fingerprint pattern, and thus in the ON-state. Suppose all other diode elements are in the OFF-state, current/voltage leak is limited to that through the adjacent first electrodes X1 and X3. The neighbor receptivity (resistivity) is $R32_{(om}+r23$ for the leak through the first electrode X3, and $R12_{(om}+r12$ for the leak through the first electrode X1, where rij is a resistance between the first electrodes Xi and Xj. If the diode element D22 is OFF and the diode element D32 is ON instead (when the second electrode Y2 is selected), and the input resistivity Rx2 from the first electrode X2 is far greater than $R32_{(O_n)}+r23$, that is, $R32_{(O_n)}+r23 \ll Rx2$, then the signal read out from the first electrode X2 into the operational amp (read circuit) is low enough such that the OFF-state read signal is lower than the sensing threshold voltage Vth such that the output from the first electrode X2 is to be read as "0". Similarly, if the diode element D12 is also ON, $(R32+r23) \times (R12+r12)/(R32+R12+r12+r23) - 1/2(R32+r23) \ll Rx2$.

Figure 30B:
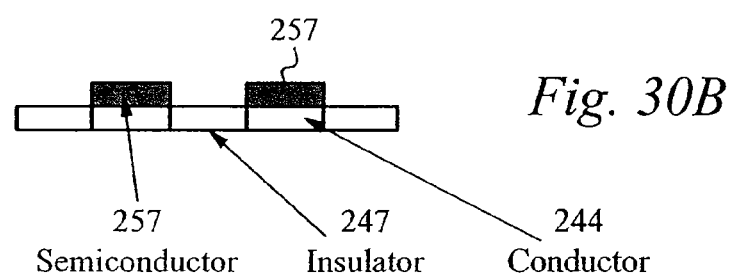
FIG. 30B is a cross-sectional diagram taken along line 30B-30B of FIG. 30A.
Figure 30A:
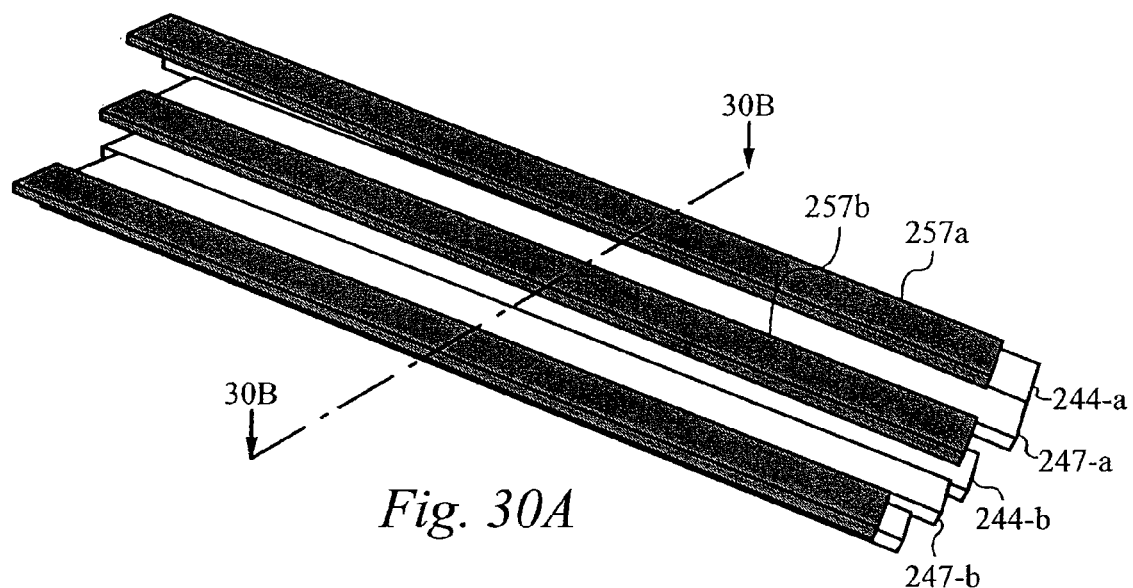
FIG. 30A is a perspective diagram schematically illustrating a biometric sensor panel in accordance with one embodiment of the present invention.

FIG. 30A is a perspective diagram schematically illustrating a biometric sensor panel in accordance with one embodiment of the present invention. FIG. 30B is a cross-sectional diagram taken along line 30B-30B of FIG. 30A. In this embodiment, the semiconductor layer 257 formed on the first electrodes 244 is patterned in strips 257-a, 257-b, ... such that the semiconductor layer 257 is only formed on the corresponding first electrode 244 (244-a, 244-b, ... ). That is, the semiconductor layer strip 257-*a* for the first electrode 244-*a* is isolated from the semiconductor layer strip 247-*b* for the first electrode 244-*b* adjacent the first electrode 244-*a*. The patterning of the semiconductor layer 257 may use a lift-off process. In addition, an insulator layer 247 is formed between adjacent first electrodes 244. Another insulator layer may also formed between adjacent second electrodes 254 (not shown). By patterning the semiconductor layer 257, crosstalk between adjacent X-lines is avoided. Strict alignment between the first and second substrates is not required, including the X-Y alignment, similarly to the embodiment of the biometric sensor panel 290 described above. However, the alignment between the semiconductor layer 257 and the first electrodes (conductor layer) 244 is necessary.

Figure 31:
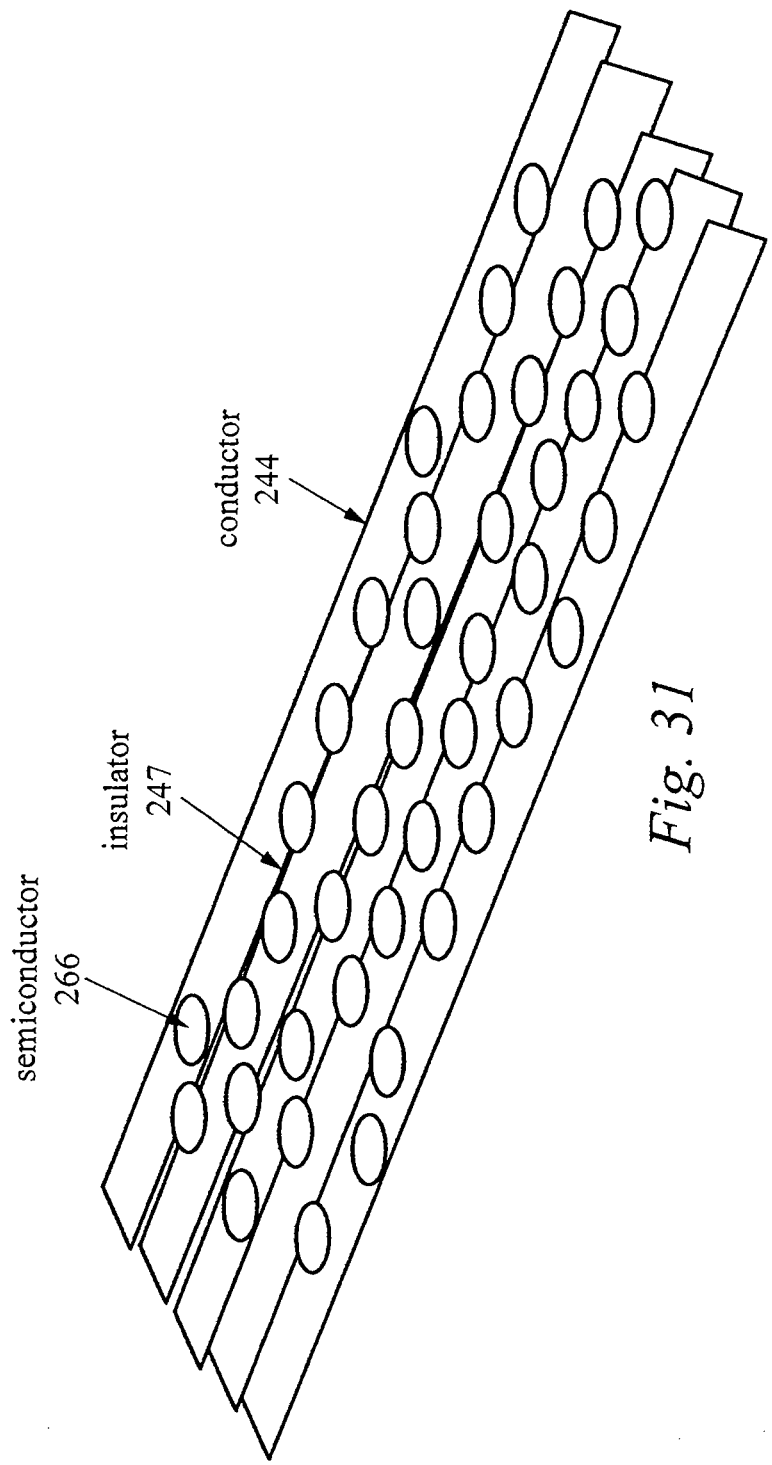
FIG. 31 is a diagram schematically illustrating another example the structure of a semiconductor layer in a biometric sensor panel in accordance with one embodiment of the present invention.

FIG. 31 is a diagram schematically illustrating another example the structure of a semiconductor layer in a biometric sensor panel in accordance with one embodiment of the present invention. In this embodiment, the semiconductor layer 266 formed on the first electrodes 244 is patterned such that the semiconductor layer 266 is consisting of small isolated portions, such as round islands (or dots), provides over the first electrodes 244. The semiconductor layer 266 may have a repeating pattern of a specific shape, such as a circle, triangle or other polygon, and the like. As long as each island is formed such that it only in contact with one electrode but not two or more electrodes, crosstalk between the adjacent electrodes is avoided.

Figure 32A:
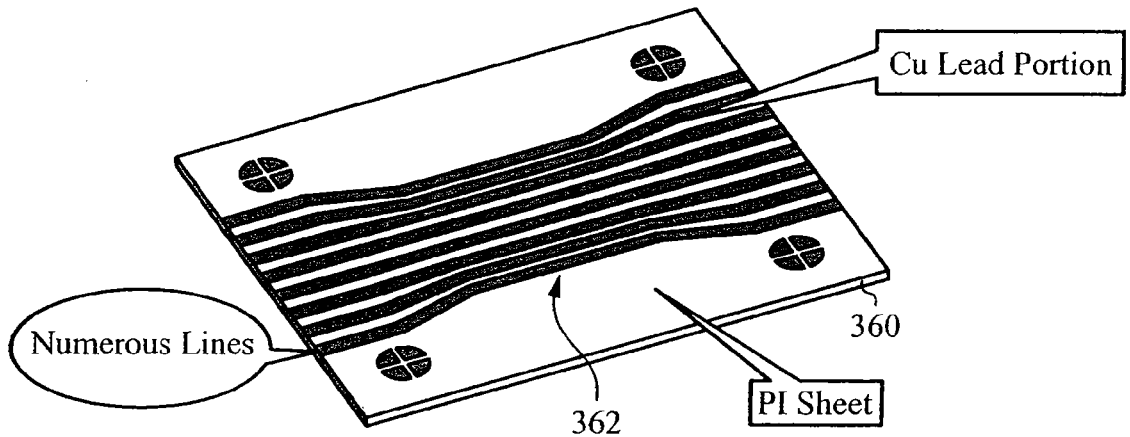
FIGS. 32A, 32B, 32C, 32D, 32E and 32F are perspective diagrams schematically illustrating a process for making electrodes for a biometric sensor panel in accordance with one embodiment of the present invention.
Figure 32B:
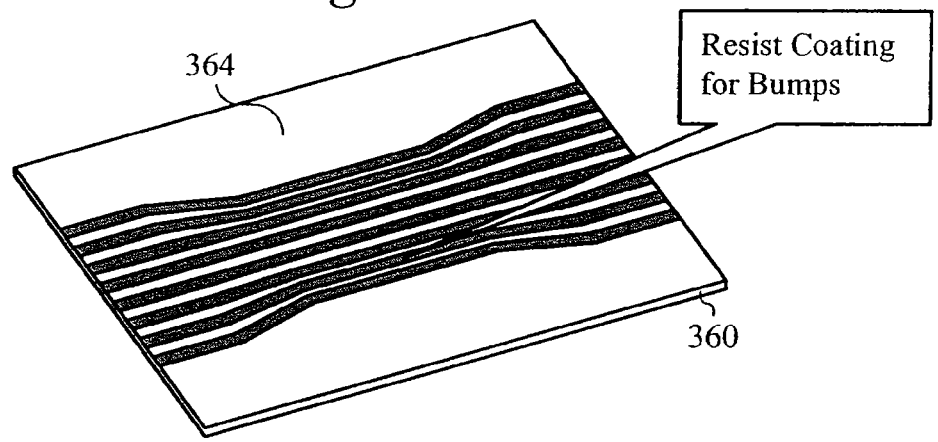
Figure 32C:
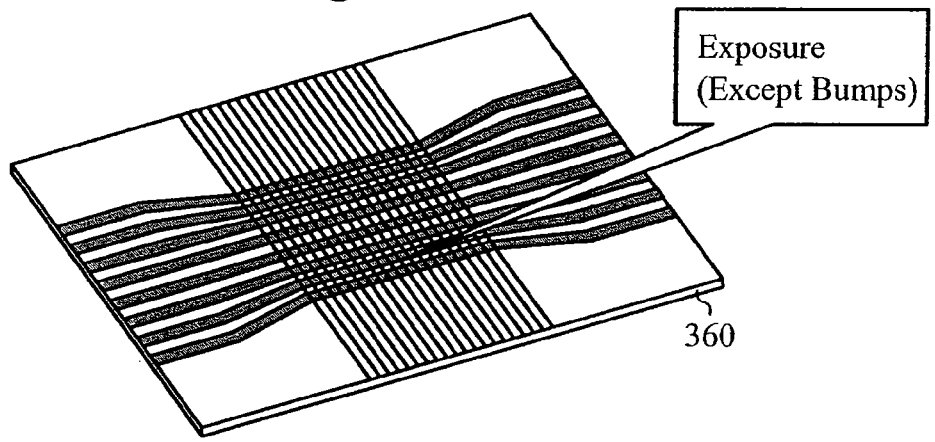
Figure 32D:
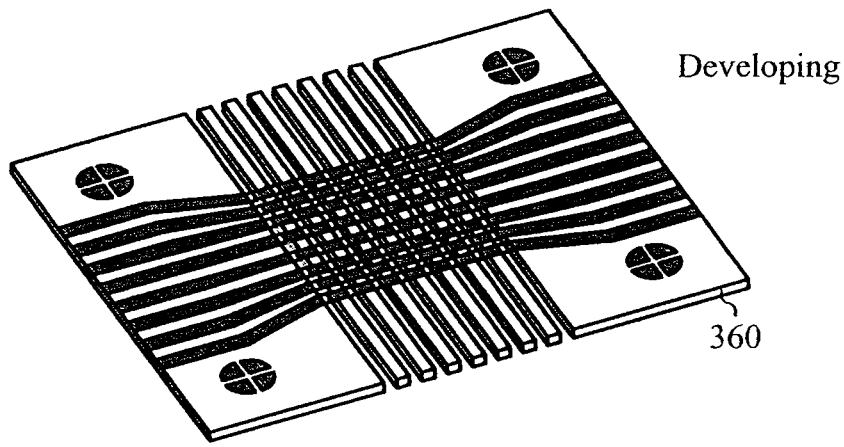
Figure 32E:
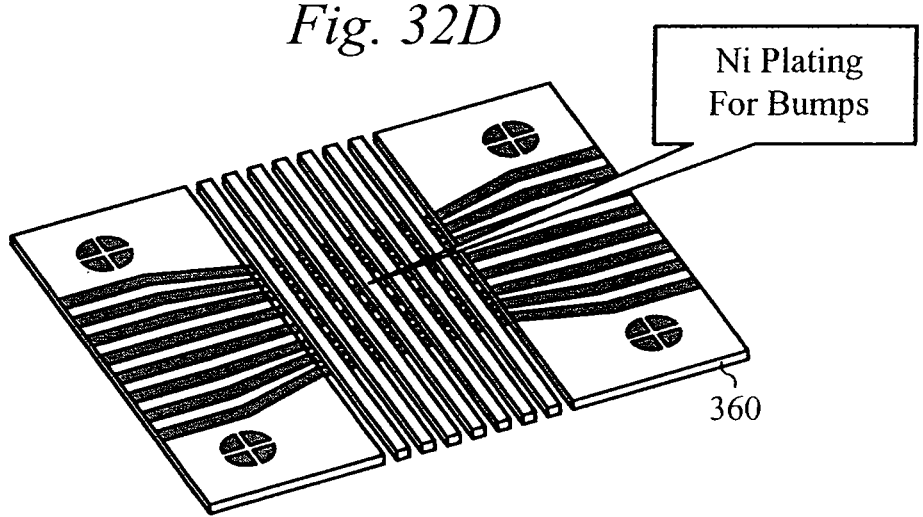
Figure 32F:
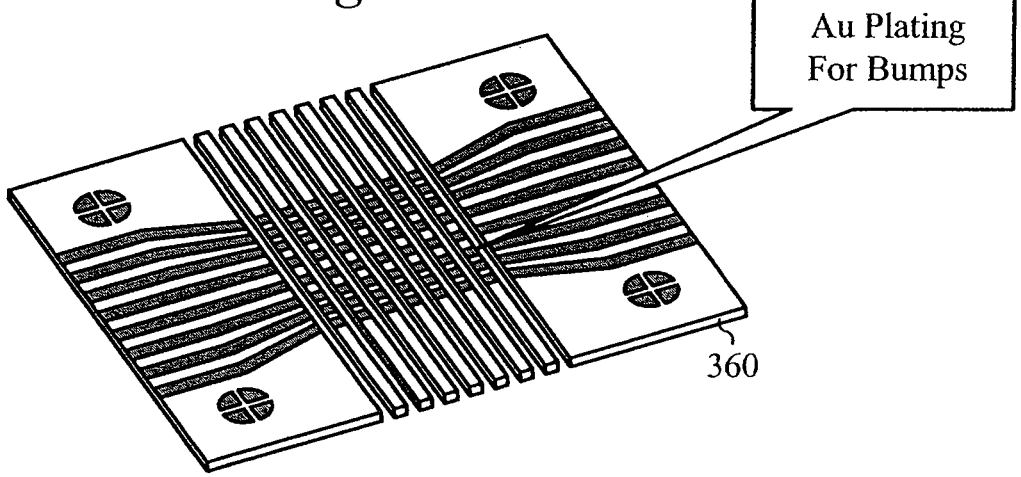
Figure 33:
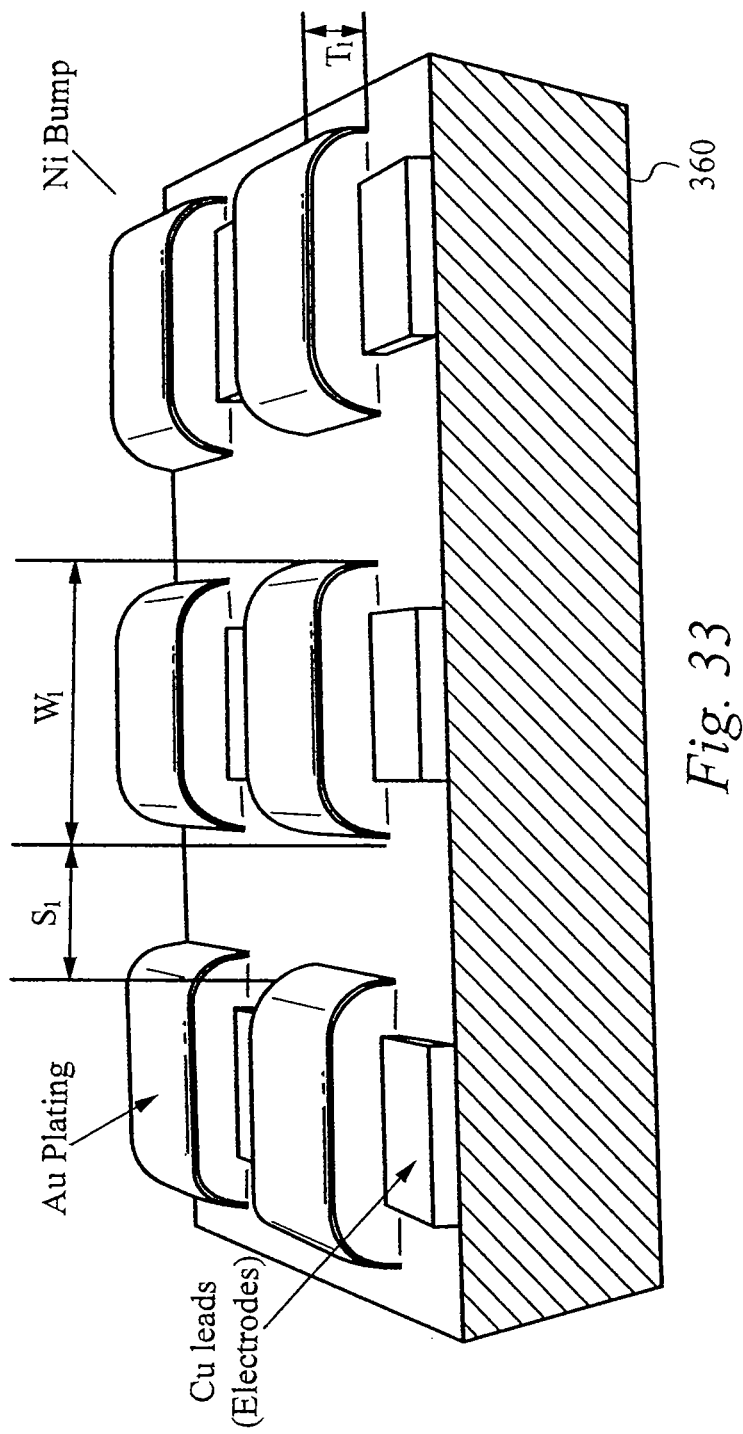
FIG. 33 is a perspective diagram schematically illustrating a system of a biometric sensor having electrodes (Cu leads) with Ni bumps having Au plating in accordance with one embodiment of the present invention.

FIGS. 32A, 32B, 32C, 32D, 32E and 32 F are perspective diagrams schematically illustrating a process for making electrodes for a biometric sensor panel in accordance with one embodiment of the present invention. A Cu layer (for example, about 2 µm thick) is formed on a flexible substrate 360 such as a polyimide sheet, and patterned into electrodes (lead lines) 362 by etching (FIG. 32A). The lead line width may be about 20 µm, and the space between the lead lines may be about 30 µm. The polyimide sheet 360 may have the thickness of about 25 µm. Then, a photo-resist layer 364 is coated on the substrate 360 (FIG. 32B), and exposed to the light except the portions to form bumps, using an appropriate photo mask (not shown) (FIG. 32C). Alternatively, a laser beam may be used to expose the photo-resist for direct patterning. Then, the photo-resist are removed by developing so as to expose the portions for bumps (FIG. 32D). An Ni layer is formed by plating so as to form bumps (FIG. 32E). For example, the thickness ($T_i$) of the Ni layer may be about 5 µm. In addition, an Au layer is formed by plating on the Ni bumps (FIG. 32F). For example, the thickness of the Au layer may be 1 µm. Preferably, the photo-resist is not removed and remain on the substrate 360 as an insulation layer. FIG. 33 schematically illustrates resulting electrodes (Cu leads) with Ni bumps having Au plating, in which the insulation layer is not shown. As shown in FIG. 33, in the portion where the bumps are formed, the width ($w_i$) of the lead line may, for example, be about 30 µm (including the original lead line width 20 µm and the bump thickness 5 µm on the both sides), and thus the spacing ($S_i$) between the lead lines maybe about 20 µm.

Variations

Some variations of that described above include:

A biometric sensor panel might comprise: a first flexible substrate; a plurality of first electrodes formed on the first flexible substrate, the first electrodes being arranged in a first direction; a second flexible substrate; a plurality of second electrodes formed on the second flexible substrate, the second electrodes being arranged in a second direction intersecting the first direction; and a plurality of sensor elements formed between the first and second electrodes at an intersection of the first and second electrodes, each of the sensor elements including: a) a diode element electrically coupled to one of the first electrodes; and b) a switching element coupled between the diode element and one of the second electrodes, the switching element allowing the second electrode to be electrically connected to the diode element if the second flexible substrate is depressed by a biometric pattern towards the first flexible substrate at the corresponding intersection.

The switching element might comprises a pressure sensitive conductive layer formed between the second electrode and the diode element, a first anisotropic conductive film (ACF) formed between the pressure sensitive conductive layer and the diode element, and/or a second ACF formed between the pressure sensitive conductive layer and the first electrode.

Each of the diode elements might include one of a p-n junction, a p+-p-n-n junction, and/or a Schottky diode and/or might have a forward drop of less than 1.0 V at an operating current.

A biometric sensor panel might comprise: a first flexible substrate; a plurality of first electrodes formed on the first flexible substrate, the first electrodes being arranged in a first direction; a second flexible substrate; a plurality of second electrodes formed on the second flexible substrate, the second electrodes being arranged in a second direction crossing the first direction; and an intermediate layer provided between the first flexible substrate and the second flexible substrate, the first electrodes and the second electrodes facing each other via the intermediate layer, the intermediate layer including: a) an insulation layer having a via hole between the first and second flexible substrate at each crossing portion of the first and second electrodes; b) a diode layer provided on the first electrode in each via hole; and c) a gap provided between the diode layer and the second electrode in each via hole, the gap allowing the second electrode to be electrically connected to the diode layer if the second flexible substrate is depressed by a biometric pattern towards the first flexible substrate at the corresponding crossing portion.

The gap can be made of an air gap allowing the second electrode to directly come into contact with the diode layer if the second flexible substrate is depressed by a biometric pattern at the corresponding crossing portion towards the first flexible substrate; a pressure-sensitive elastic resistive layer which became conductive when depressed; or a reversible anisotropic conductive film (ACF). The diode layer can include one of a PN junction, a PIN junction, and/or a metal-semiconductor junction, and/or the diode layer is made of a P-type semiconducting polymer layer and an N-type semiconducting polymer layer.

The second electrode might include a conductive bump provided thereon facing the diode layer in each via hole. The biometric sensor panel may further comprise a back layer having a plurality of bumps provided thereon, each of the bumps contacting with the first flexible substrate at a location aligned with a via hole. The bumps might push the first electrode towards the second electrode from the first flexible substrate side when the second flexible substrate at the corresponding via hole is depressed by a biometric pattern.

In a method for detecting a biometric pattern using a biometric sensor panel, the method might receiving a pressure on a second flexible substrate from a biometric pattern, the second flexible substrate deforming in accordance with the biometric pattern, the gap allowing a second electrode to be electrically connected to a diode layer if the second flexible substrate is depressed at a corresponding sensor element towards a first flexible substrate, driving the plurality of second electrodes in accordance with a first timing, driving the plurality of first electrodes in accordance with a second timing for each of the plurality of first electrodes which is being driven, and reading out an electric signal from each of the sensor element through the first electrodes. The gap might be made of either one of an air gap allowing the second electrode to directly come into contact with the diode layer if the second flexible substrate is depressed at the corresponding sensor element towards the first flexible substrate, a pressure-sensitive elastic resistive layer which became conductive when depressed, and/or a reversible anisotropic conductive film (ACF).

The sensor might include an intermediate layer on the first flexible substrate provided with the first electrodes made by applying a photo-setting resin over the first flexible substrate provided with the plurality of first electrodes, curing the photo-setting resin by irradiation of light using a photo-mask having a pattern for the sensor elements to be formed, removing the photo-mask and the uncured portion of the photo-setting resin, the cured photo-setting resin forming an insulation layer having via holes to the first electrodes at locations for the sensor elements, providing a diode layer in the via holes, providing a gap layer on the diode layer in the via holes, and providing a second flexible substrate and a plurality of second electrodes arranged in a second direction on the second flexible substrate such that the second electrodes face the first electrodes via the intermediate layer, and the first and second electrodes cross each other at the sensor element locations.

The plurality of second electrodes might include depositing a conductive material layer on the second flexible substrate and patterning the conductive material layer into the plurality of second electrodes. The diode layer might include providing an N-type semiconducting polymer into the via holes and/or providing a P-type semiconducting polymer into the via holes. The semiconducting polymers might include ink-jet printing the type semiconducting polymer into the via holes and/or spin-coating and doctor-blading the semiconducting polymer.

While embodiments and applications of this invention have been shown and described, it would be apparent to those skilled in the art having the benefit of this disclosure that many more modifications than mentioned above are possible without departing from the inventive concepts herein. The invention, therefore, is not to be restricted except in the spirit of the appended claims.

What is claimed is:

1. A biometric sensor panel, comprising:
  a first flexible substrate;
  a plurality of first electrodes formed on the first flexible substrate, the first electrodes being arranged in a first direction;
  a first insulation layer formed on the first electrodes over the first flexible substrate;
  a plurality of first contact pads formed on the first insulation layer, the first contact pads aligned with the first electrodes and connected to corresponding ones of the first electrodes through vias formed in the first insulation layer;
  a semiconductor layer formed on the first contact pads over the first insulation layer;
  a second flexible substrate;
  a plurality of second electrodes formed on the second flexible substrate, the second electrodes being arranged in a second direction crossing the first direction;
  a second insulation layer formed on the second electrodes over the second flexible substrate;
  a plurality of second contact pads formed on the second insulation layer, the second contact pads aligned with the second electrodes and connected to corresponding ones of the second electrodes through vias formed in the second insulation layer; and
  a pressure sensitive conductive layer, wherein the first and second flexible substrates face each other such that each of the first contact pads is aligned with a corresponding one of the second contact pads via the semiconductor layer and the pressure sensitive conductive layer sandwiched therebetween.

2. The biometric sensor panel of claim 1, further comprising:
  a first anisotropic conductive film ("ACF") formed on the pressure sensitive conductive layer connecting the semiconductor layer and the pressure sensitive conductive layer; and
  a second anisotropic conductive film ("ACF") formed on the pressure sensitive conductive layer connecting the second contact pads and the pressure sensitive conductive layer.

3. The biometric sensor panel of claim 1, wherein each of the first and second contact pads is formed in a bump shape protruding toward the pressure sensitive conductive layer.

4. The biometric sensor panel of claim 1, wherein a thickness of the first contact pads is greater than a thickness of the semiconductor layer such that each part of the semiconductor layer formed on the first contact pads is isolated from the remaining part of the semiconductor layer formed directly on the first insulation layer.

5. A biometric sensor panel, comprising:
  a first flexible substrate;
  a plurality of first electrodes formed on the first flexible substrate, the first electrodes being arranged in a first direction;
  a second flexible substrate;
  a plurality of second electrodes formed on the second flexible substrate, the second electrodes being arranged in a second direction crossing the first direction; and
  an intermediate layer provided between the first flexible substrate and the second flexible substrate, the first electrodes and the second electrodes facing each other via the intermediate layer, the intermediate layer including:
    a) an insulation layer having a via hole between the first and second flexible substrate at each crossing portion of the first and second electrodes;
    b) a diode layer formed in the insulating layer, the diode layer provided on the first electrode in each via hole, the insulation layer and the diode layer forming a diode matrix layer;
    c) an anisotropic conductive film (ACF) formed on the diode matrix layer; and
    d) a pressure sensitive conductive layer formed on the ACF, the pressure sensitive conductive layer allowing the second electrode to be electrically connected to the diode layer via the ACF if the second flexible substrate is depressed by a biometric pattern towards the first flexible substrate at the corresponding crossing portion.

6. A biometric sensor panel, comprising:
  a first flexible substrate;
  a plurality of first electrodes formed on the first flexible substrate, the first electrodes being arranged in a first direction;
  a second flexible substrate;
  a plurality of second electrodes formed on the second flexible substrate, the second electrodes being arranged in a second direction crossing the first direction; and an intermediate layer provided between the first flexible substrate and the second flexible substrate, the first electrodes and the second electrodes facing each other via the intermediate layer, the intermediate layer including:
  a) a diode array formed on the first electrodes, the diode array including a plurality of vertical diode elements provided at crossing portions of the first and second electrodes;
  b) an anisotropic conductive film (ACF) formed on the diode array; and
  c) a pressure sensitive conductive layer formed on the ACF, the pressure sensitive conductive layer allowing the second electrode to be electrically connected to a diode element of the diode array via the ACF if the second flexible substrate is depressed by a biometric pattern towards the first flexible substrate at the corresponding crossing portion.

7. The biometric sensor panel of claim 6, wherein each of the diode elements includes one of a p-n junction, a p+-p-n-n junction and/or a Schottky diode.

8. The biometric sensor panel of claim 6, further comprising an insulation layer provided between the ACF and the first flexible substrate so as to fill spaces between the diode elements.

9. The biometric sensor panel of claim 6, further comprising a second ACF formed on the pressure sensitive conductive layer.

10. The biometric sensor panel of claim 6, wherein each of the diode elements has a forward drop of less than 1.0 V at an operating current.

* * * * *